(12) United States Patent
Sharvit et al.

(10) Patent No.: US 9,198,791 B2
(45) Date of Patent: Dec. 1, 2015

(54) PANCREATICOBILIARY DIVERSION DEVICE

(75) Inventors: Pierre Sharvit, Hefer (IL); Chen Porat, Kiryat Tivon (IL); Dan Kinarty, Haifa (IL); Roni Zvuloni, Haifa (IL)

(73) Assignee: ENDOBETIX LTD., Israel (IL)

( * ) Notice: Subject to any disclaimer, the term of this patent is extended or adjusted under 35 U.S.C. 154(b) by 140 days.

(21) Appl. No.: 13/811,333

(22) PCT Filed: Jul. 20, 2011

(86) PCT No.: PCT/IL2011/000579
§ 371 (c)(1),
(2), (4) Date: Mar. 27, 2013

(87) PCT Pub. No.: WO2012/011105
PCT Pub. Date: Jan. 26, 2012

(65) Prior Publication Data
US 2013/0197421 A1 Aug. 1, 2013

Related U.S. Application Data

(60) Provisional application No. 61/366,586, filed on Jul. 22, 2010.

(51) Int. Cl.
*A61F 2/02* (2006.01)
*A61F 2/04* (2013.01)
(Continued)

(52) U.S. Cl.
CPC .............. *A61F 5/0036* (2013.01); *A61F 2/04* (2013.01); *A61F 5/0003* (2013.01);
(Continued)

(58) Field of Classification Search
CPC ....... A61F 2/04; A61F 5/0036; A61F 5/0076; A61F 2/88; A61F 2002/045; A61F 2002/04; A61F 2002/041; A61F 2002/044; A61F 2002/848; A61F 2002/8483; A61F 2002/8486; A61F 5/0003; A61F 5/0013; A61F 5/0079; A61M 27/002; A61M 2210/1042; A61M 2210/1053; A61M 2210/1057; A61M 2210/106
See application file for complete search history.

(56) References Cited

U.S. PATENT DOCUMENTS

| 4,315,509 A | 2/1982 | Smit |
| 4,823,808 A | 4/1989 | Clegg et al. |

(Continued)

FOREIGN PATENT DOCUMENTS

| WO | 98/23242 A2 | 6/1998 |
| WO | 99/62431 A1 | 12/1999 |

(Continued)

OTHER PUBLICATIONS

Extended European Search Report issued in corresponding European Application No. 11809372.3 dated Dec. 2, 2013 (6 pages).
(Continued)

*Primary Examiner* — Adam Marcetich
(74) *Attorney, Agent, or Firm* — Sughrue Mion, PLLC

(57) ABSTRACT

Apparatus (20) for use with pancreaticobiliary secretions that enter a gastrointestinal tract of a subject at an anatomical entry location, the apparatus (20) comprising: a pancreaticobiliary secretion-diversion guide (30) configured to collect the pancreaticobiliary secretions from the anatomical entry location and deliver the pancreaticobiliary secretions to a location in the gastrointestinal tract that is distal to the anatomical entry location; and an anchoring system (40) comprising one or more helical anchors (80) located within the gastrointestinal tract and configured to apply pressure to a wall of the gastrointestinal tract in order to maintain the pancreaticobiliary secretion-diversion guide in place.

24 Claims, 10 Drawing Sheets

(51) Int. Cl.
  *A61F 5/00* (2006.01)
  *A61M 27/00* (2006.01)
  *A61F 2/848* (2013.01)
  *A61F 2/88* (2006.01)

(52) U.S. Cl.
  CPC ............ *A61F 5/0013* (2013.01); *A61F 5/0076* (2013.01); *A61F 5/0079* (2013.01); *A61M 27/002* (2013.01); *A61F 2/848* (2013.01); *A61F 2/88* (2013.01); *A61F 2002/041* (2013.01); *A61F 2002/044* (2013.01); *A61F 2002/045* (2013.01); *A61M 2210/106* (2013.01); *A61M 2210/1042* (2013.01); *A61M 2210/1053* (2013.01); *A61M 2210/1057* (2013.01)

(56) References Cited

U.S. PATENT DOCUMENTS

| | | | |
|---|---|---|---|
| 4,878,905 A | 11/1989 | Blass | |
| 5,226,429 A | 7/1993 | Kuzmak | |
| 5,306,300 A | 4/1994 | Berry | |
| 5,443,498 A * | 8/1995 | Fontaine | 623/1.17 |
| 5,540,701 A * | 7/1996 | Sharkey et al. | 606/153 |
| 5,820,584 A | 10/1998 | Crabb | |
| 6,656,194 B1 | 12/2003 | Gannoe et al. | |
| 6,746,460 B2 | 6/2004 | Gannoe et al. | |
| 6,755,869 B2 | 6/2004 | Geitz | |
| 6,981,978 B2 | 1/2006 | Gannoe | |
| 6,994,095 B2 | 2/2006 | Burnett | |
| 6,994,715 B2 | 2/2006 | Gannoe et al. | |
| 7,025,791 B2 | 4/2006 | Levine et al. | |
| 7,033,373 B2 | 4/2006 | Torre et al. | |
| 7,033,384 B2 | 4/2006 | Gannoe et al. | |
| 7,122,058 B2 | 10/2006 | Levine et al. | |
| 7,175,669 B2 | 2/2007 | Geitz | |
| 7,211,094 B2 | 5/2007 | Gannoe et al. | |
| 7,211,114 B2 | 5/2007 | Bessler et | |
| 7,214,233 B2 | 5/2007 | Gannoe et al. | |
| 7,220,284 B2 | 5/2007 | Kagan et al. | |
| 7,267,694 B2 | 9/2007 | Levine et al. | |
| 7,314,489 B2 | 1/2008 | McKenna et al. | |
| 7,329,285 B2 | 2/2008 | Levine et al. | |
| 7,347,868 B2 | 3/2008 | Burnett et al. | |
| 7,347,875 B2 | 3/2008 | Levine et al. | |
| 7,476,256 B2 | 1/2009 | Meade et al. | |
| 7,608,114 B2 | 10/2009 | Levine et al. | |
| 7,678,068 B2 | 3/2010 | Levine et al. | |
| 7,682,330 B2 | 3/2010 | Meade et al. | |
| 7,695,446 B2 | 4/2010 | Levine et al. | |
| 7,753,870 B2 | 7/2010 | Demarais et al. | |
| 7,753,928 B2 | 7/2010 | Torre et al. | |
| 7,758,535 B2 | 7/2010 | Levine et al. | |
| 7,766,861 B2 | 8/2010 | Levine et al. | |
| 7,766,973 B2 | 8/2010 | Levine et al. | |
| 7,771,382 B2 | 8/2010 | Levine et al. | |
| 7,815,589 B2 | 10/2010 | Meade et al. | |
| 7,815,591 B2 | 10/2010 | Levine et al. | |
| 7,819,836 B2 | 10/2010 | Levine et al. | |
| 7,833,279 B2 | 11/2010 | Knudson et al. | |
| 7,837,643 B2 | 11/2010 | Levine et al. | |
| 7,837,645 B2 | 11/2010 | Bessler et al. | |
| 7,837,669 B2 | 11/2010 | Dann et al. | |
| 7,867,283 B2 | 1/2011 | Krueger et al. | |
| 7,881,797 B2 | 2/2011 | Griffin et al. | |
| 7,892,214 B2 | 2/2011 | Kagan et al. | |
| 7,922,684 B2 | 4/2011 | Weitzner et al. | |
| 7,931,693 B2 | 4/2011 | Binmoeller | |
| 7,935,073 B2 | 5/2011 | Levine et al. | |
| 7,947,055 B2 | 5/2011 | Gannoe et al. | |
| 7,976,488 B2 | 7/2011 | Levine et al. | |
| 7,981,163 B2 | 7/2011 | Meade et al. | |
| 8,007,507 B2 | 8/2011 | Waller | |
| 8,038,720 B2 | 10/2011 | Wallace et al. | |
| 8,048,169 B2 | 11/2011 | Burnett et al. | |
| 8,057,420 B2 | 11/2011 | Meade et al. | |
| 8,062,207 B2 | 11/2011 | Gannoe et al. | |
| 8,083,756 B2 | 12/2011 | Gannoe et al. | |
| 8,083,757 B2 | 12/2011 | Gannoe et al. | |
| 8,092,482 B2 | 1/2012 | Gannoe et al. | |
| 8,096,966 B2 | 1/2012 | Levine et al. | |
| 8,109,895 B2 | 2/2012 | Williams et al. | |
| 8,137,301 B2 | 3/2012 | Levine et al. | |
| 8,142,385 B2 | 3/2012 | Grau et al. | |
| 8,142,513 B2 | 3/2012 | Shalon et al. | |
| 8,147,561 B2 | 4/2012 | Binmoeller | |
| 8,162,871 B2 | 4/2012 | Levine et al. | |
| 8,182,441 B2 | 5/2012 | Swain et al. | |
| 8,226,593 B2 | 7/2012 | Graham et al. | |
| 8,303,669 B2 | 11/2012 | Meade et al. | |
| 8,323,229 B2 | 12/2012 | Shin et al. | |
| 8,337,567 B2 | 12/2012 | Stack et al. | |
| 8,366,650 B2 | 2/2013 | Young | |
| 8,372,158 B2 | 2/2013 | Levy et al. | |
| 8,376,981 B2 | 2/2013 | Laufer | |
| 8,403,877 B2 | 3/2013 | Priplata et al. | |
| 8,403,952 B2 | 3/2013 | Brooks et al. | |
| 8,414,559 B2 | 4/2013 | Gross | |
| 2002/0055757 A1 | 5/2002 | De la Torre et al. | |
| 2003/0070676 A1* | 4/2003 | Cooper et al. | 128/200.24 |
| 2004/0030347 A1 | 2/2004 | Gannoe et al. | |
| 2004/0039452 A1* | 2/2004 | Bessler | 623/23.65 |
| 2004/0044357 A1 | 3/2004 | Gannoe et al. | |
| 2004/0088008 A1 | 5/2004 | Gannoe et al. | |
| 2004/0093091 A1 | 5/2004 | Gannoe et al. | |
| 2004/0220682 A1 | 11/2004 | Levine et al. | |
| 2004/0249362 A1 | 12/2004 | Levine et al. | |
| 2004/0267377 A1 | 12/2004 | Egle | |
| 2005/0033331 A1 | 2/2005 | Burnett et al. | |
| 2005/0043817 A1 | 2/2005 | McKenna et al. | |
| 2005/0049718 A1 | 3/2005 | Dann et al. | |
| 2005/0055039 A1 | 3/2005 | Burnett et al. | |
| 2005/0075622 A1 | 4/2005 | Levine et al. | |
| 2005/0080395 A1 | 4/2005 | Levine et al. | |
| 2005/0080491 A1 | 4/2005 | Levine et al. | |
| 2005/0085787 A1 | 4/2005 | Laufer | |
| 2005/0085923 A1 | 4/2005 | Levine et al. | |
| 2005/0096750 A1 | 5/2005 | Kagan et al. | |
| 2005/0125020 A1 | 6/2005 | Meade et al. | |
| 2005/0125075 A1 | 6/2005 | Meade et al. | |
| 2005/0192614 A1 | 9/2005 | Binmoeller | |
| 2005/0192615 A1 | 9/2005 | Torre et al. | |
| 2005/0222592 A1 | 10/2005 | Gannoe et al. | |
| 2005/0240279 A1 | 10/2005 | Kagan et al. | |
| 2005/0247320 A1 | 11/2005 | Stack et al. | |
| 2006/0009858 A1 | 1/2006 | Levine et al. | |
| 2006/0020278 A1 | 1/2006 | Burnett et al. | |
| 2006/0069400 A1 | 3/2006 | Burnett et al. | |
| 2006/0106332 A1 | 5/2006 | Knudson et al. | |
| 2006/0135963 A1 | 6/2006 | Kick et al. | |
| 2006/0161187 A1 | 7/2006 | Levine et al. | |
| 2006/0178691 A1 | 8/2006 | Binmoeller | |
| 2006/0190019 A1 | 8/2006 | Gannoe et al. | |
| 2007/0005147 A1 | 1/2007 | Levine et al. | |
| 2007/0038308 A1 | 2/2007 | Geitz | |
| 2007/0083224 A1 | 4/2007 | Hively | |
| 2007/0083271 A1 | 4/2007 | Levine et al. | |
| 2007/0156248 A1 | 7/2007 | Marco et al. | |
| 2007/0173869 A1 | 7/2007 | Gannoe et al. | |
| 2007/0250020 A1 | 10/2007 | Kim et al. | |
| 2007/0250132 A1 | 10/2007 | Burnett | |
| 2007/0265709 A1 | 11/2007 | Rajan et al. | |
| 2007/0282418 A1* | 12/2007 | Weitzner | 623/1.11 |
| 2007/0282452 A1 | 12/2007 | Weitzner et al. | |
| 2007/0282453 A1 | 12/2007 | Weitzner et al. | |
| 2007/0282454 A1 | 12/2007 | Krueger et al. | |
| 2007/0293885 A1 | 12/2007 | Binmoeller | |
| 2008/0033574 A1* | 2/2008 | Bessler et al. | 623/23.68 |
| 2008/0051823 A1 | 2/2008 | Makower et al. | |
| 2008/0051824 A1 | 2/2008 | Gertner | |
| 2008/0058840 A1* | 3/2008 | Albrecht et al. | 606/153 |
| 2008/0065136 A1 | 3/2008 | Young | |
| 2008/0188766 A1 | 8/2008 | Gertner | |
| 2008/0208241 A1 | 8/2008 | Weiner et al. | |
| 2008/0208357 A1 | 8/2008 | Melanson et al. | |

(56) References Cited

U.S. PATENT DOCUMENTS

| | | |
|---|---|---|
| 2008/0221702 A1 | 9/2008 | Wallace et al. |
| 2008/0228126 A1* | 9/2008 | Bessler ............................ 604/9 |
| 2008/0234834 A1 | 9/2008 | Meade et al. |
| 2008/0249635 A1 | 10/2008 | Weitzner et al. |
| 2008/0255476 A1 | 10/2008 | Boyajian et al. |
| 2008/0300618 A1 | 12/2008 | Gertner |
| 2009/0012553 A1 | 1/2009 | Swain et al. |
| 2009/0036910 A1 | 2/2009 | Kim et al. |
| 2009/0062717 A1 | 3/2009 | Laufer |
| 2009/0118757 A1 | 5/2009 | Burnett et al. |
| 2009/0143713 A1 | 6/2009 | Van Dam et al. |
| 2009/0187206 A1 | 7/2009 | Binmoeller et al. |
| 2009/0216337 A1 | 8/2009 | Egan et al. |
| 2009/0240340 A1 | 9/2009 | Levine et al. |
| 2009/0248171 A1 | 10/2009 | Levine et al. |
| 2009/0264808 A1 | 10/2009 | Young |
| 2009/0299486 A1 | 12/2009 | Shohat et al. |
| 2009/0299487 A1* | 12/2009 | Stack et al. ................ 623/23.65 |
| 2010/0023110 A1 | 1/2010 | Schaeffer |
| 2010/0076543 A1 | 3/2010 | Melsheimer et al. |
| 2010/0114150 A1* | 5/2010 | Magal ........................... 606/192 |
| 2010/0191167 A1* | 7/2010 | Laufer ............................ 604/8 |
| 2010/0256776 A1 | 10/2010 | Levine et al. |
| 2010/0286628 A1 | 11/2010 | Gross |
| 2010/0286660 A1 | 11/2010 | Gross |
| 2010/0298632 A1 | 11/2010 | Levine et al. |
| 2010/0305590 A1 | 12/2010 | Holmes et al. |
| 2010/0331756 A1 | 12/2010 | Meade et al. |
| 2011/0046537 A1 | 2/2011 | Errico et al. |
| 2011/0066175 A1 | 3/2011 | Gross |
| 2011/0100381 A1 | 5/2011 | Elmer et al. |
| 2011/0106020 A1 | 5/2011 | Elmer et al. |
| 2011/0106225 A1* | 5/2011 | Elmer et al. .................... 607/96 |
| 2011/0137227 A1 | 6/2011 | McKinley et al. |
| 2011/0166556 A1 | 7/2011 | Shalon |
| 2011/0172584 A1 | 7/2011 | Chin |
| 2011/0190684 A1 | 8/2011 | Binmoeller |
| 2011/0245752 A1 | 10/2011 | Levine et al. |
| 2011/0257580 A1 | 10/2011 | Meade et al. |
| 2011/0276091 A1 | 11/2011 | Melanson et al. |
| 2011/0301523 A1 | 12/2011 | Levine et al. |
| 2011/0307075 A1* | 12/2011 | Sharma ....................... 623/23.65 |
| 2012/0041465 A1 | 2/2012 | Shalon |
| 2012/0172999 A1 | 7/2012 | Binmoeller |
| 2012/0221037 A1* | 8/2012 | Birk et al. ..................... 606/191 |
| 2013/0030350 A1 | 1/2013 | Albrecht et al. |
| 2013/0030351 A1 | 1/2013 | Belhe et al. |
| 2013/0079603 A1 | 3/2013 | Vargas |

FOREIGN PATENT DOCUMENTS

| | | |
|---|---|---|
| WO | 01/19231 A2 | 3/2001 |
| WO | 02/04040 A2 | 1/2002 |
| WO | 02/089869 A2 | 11/2002 |
| WO | 03/022325 A2 | 3/2003 |
| WO | 2004/049982 A2 | 6/2004 |
| WO | 2004/087014 A2 | 10/2004 |
| WO | 2004/087233 A2 | 10/2004 |
| WO | 2005/060869 A1 | 7/2005 |
| WO | 2005/060882 A1 | 7/2005 |
| WO | 2006/016894 A1 | 2/2006 |
| WO | 2006/034062 A1 | 3/2006 |
| WO | 2006/078781 A1 | 7/2006 |
| WO | 2006/078927 A1 | 7/2006 |
| WO | 2006/102012 A1 | 9/2006 |
| WO | 2006/133311 A2 | 12/2006 |
| WO | 2007/050628 A2 | 5/2007 |
| WO | 2007/142833 A1 | 12/2007 |
| WO | 2008/121831 A1 | 10/2008 |
| WO | 2008/154450 A1 | 12/2008 |
| WO | 2009/085107 A1 | 7/2009 |
| WO | 2010/128495 A1 | 11/2010 |
| WO | 2011/031981 A1 | 3/2011 |
| WO | 2011/151830 A2 | 12/2011 |
| WO | 2012/011105 A2 | 1/2012 |
| WO | 2013/108258 A2 | 7/2013 |

OTHER PUBLICATIONS

Specification of U.S. Appl. No. 61/366,586, filed on Jul. 22, 2010 (64 pages).
Specification of U.S. Appl. No. 61/588,371, filed on Jan. 19, 2012 (79 pages).
Specification of U.S. Appl. No. 61/832,195, filed on Jun. 7, 2013 (20 pages).
International Search Report and Written Opinon issued in corresponding International Application No. PCT/IL2011/000579 dated Feb. 24, 2012 (21 pages).
International Preliminary Report on Patentability issued in corresponding International Application No. PCT/IL2011/000579 dated Jan. 22, 2013 (14 pages).
International Search Report and Written Opinon issued in corresponding International Application No. PCT/IL2013/050054 dated May 10, 2013 (12 pages).
American Diabetes Association. "Diagnosis and Classification of Diabetes Mellitus." Diabetes Care, vol. 29, Supplement 1, Jan. 2006, pp. S43-S48 (6 pages).
Armand, Martine. "Lipases and lipolysis in the human digestive tract: where do we stand?", Curr Opin Clin Nutr Metab Care, 10:156-164 (9 pages), published 2007.
Buchwald et al., "Bariatric Surgery: A Systematic Review and Meta-analysis," JAMA, vol. 292, No. 14, Oct. 13, 2004, pp. 1724-1737 (14 pages).
Cottrell et al., "Tension Receptors with Vagal Afferent Fibres in the Proximal Duodenum and Pyloric Sphincter of Sheep," Journal of Physiology, vol. 354, 1984, pp. 457-475 (19 pages).
Weyer et al., "The natural history of insulin secretory dysfunction and insulin resistance in the pathogenesis of type 2 diabetes mellitus," The Journal of Clinical Investigation, vol. 104, No. 6, Sep. 1999, pp. 787-794 (8 pages).
Ermini et al., "The Effects of Bilio-jejunal Diversion on Streptozotocin Diabetes in the Rat," Acta Diabetologica Latina, vol. 28, 1991, pp. 79-89 (11 pages).
Yilmaz et al., "Orlistat accelerates gastric emptying and attenuates GIP release in healthy subjects," Am J Physiol Gastrointest Liver Physiol, vol. 296, Dec. 24, 2008, pp. 482-489 (9 pages).
Flatt, Peter. "Effective surgical treatment of obesity may be mediated by ablation of the lipogenic gut hormone gastric inhibitory polypeptide (GIP): evidence and clinical opportunity for development of new obesity-diabetes drugs?" Diabetes and Vascular Disease Research, vol. 4, Issue 2, Jun. 2007, pp. 150-152 (4 pages).
Flatt, Peter. "Gastric inhibitory polypeptide (GIP) revisited: a new therapeutic target for obesity-diabetes?" Diabetic Medicine, vol. 25, 2008, pp. 759-764 (6 pages).
Gersin et al., "Duodenal Jejunal Bypass Sleeve: A Totally Endoscopic Device for the Treatment of Morbid Obesity" Surgical Innovation, vol. 14, No. 4, Dec. 2007, pp. 275-278 (5 pages).
Getty-Kaushik et al., "Glucose-Dependent Insulinotropic Polypeptide Modulates Adipocyte Lipolysis and Reesterification," Obesity, vol. 14, No. 7, Jul. 2006, pp. 1124-1131 (8 pages).
Imamura et al., "Effects of the Pathway of Bile Flow on the Digestion of Fat and the Release of Gastrointestinal Hormones," The American Journal of Gastroenterology, vol. 83, No. 4, Apr. 1988, pp. 386-392 (8 pages).
Jansen, Peter. "A new life for bile acids," Journal of Hepatology, vol. 52, 2010, pp. 937-938 (2 pages).
Kindel et al., "Duodenal-Jejunal Exclusion Improves Glucose Tolerance in the Diabetic, Goto-Kakizaki Rat by a GLP-1 Receptor-Mediated Mechanism," J Gastrointest Surg, vol. 13, 2009, pp. 1762-1772 (11 pages).
Klausner et al., "Expandable gastroretentive dosage forms," Journal of Controlled Release, vol. 90, 2003, pp. 143-162 (20 pages).
Knop, Filip. "Bile-induced secretion of glucagon-like peptide-1: Pathophysiological implications in type 2 diabetes?" The American Journal of Physiology—Endocrinology and Metabolism, 2010 (11 pages).

(56) References Cited

OTHER PUBLICATIONS

Lingenfelser et al., "Effects of duodenal distension on antropyloroduodenal pressures and perception are modified by hyperglycemia," American Journal of Physiology, 1999, pp. G711-G718 (8 pages).

Manfredini et al., "Internal biliary diversion improves glucose tolerance in the rat," American Journal of Physiology, 1985, pp. G519-G527 (9 pages).

McClean et al., "GIP receptor antagonism reverses obesity, insulin resistance, and associated metabolic disturbances induced in mice by prolonged consumption of high-fat diet," Am J Physiol Endocrinol Metab, vol. 293, 2007, pp. E1746-E1755 (11 pages).

Miyawaki et al., "Inhibition of gastric inhibitory polypeptide signaling prevents obesity," Nature Medicine, vol. 8, No. 7, Jul. 2002, pp. 738-742 (5 pages).

Rubino et al., "The Early Effect of the Roux-en-Y Gastric Bypass on Hormones Involved in Body Weight Regulation and Glucose Metabolism," Annals of Surgery, vol. 240, No. 2, Aug. 2004, pp. 236-242 (7 pages).

Rubino, Francesco. "Bariatric surgery: effects on glucose homeostasis," Curr. Opin. Clin. Nutr. Metab. Care., vol. 9, 2006, pp. 497-507 (Abstract only) (1 page).

Rundback et al., "Permanent or temporary IVC filtration with a novel double-ring anchoring technology optional nitinol filter," Expert Reviews Medical Devices 7(1), 2010, pp. 11-19 (9 pages).

Shafik et al., "Study of the duodenal contractile activity during antral contractions," World Journal of Gastroenterology, May 14, 2007, pp. 2600-2603 (4 pages).

Strader et al., "Weight loss through ileal transposition is accompanied by increased ileal hormone secretion and synthesis in rats," Am J Physiol Endocrinol Metab, vol. 288, 2005, pp. E447-E453 (7 pages).

Takahashi et al., "Chronic Diversion of Bile to the Urinary Bladder Induces Pancreatic Growth in Dogs," Journal of Gastrointestinal Surgery, vol. 4, No. 5, 2000, pp. 513-519 (7 pages).

Trauner et al., "Bile Acids as Regulators of Hepatic Lipid and Glucose Metabolism," Digestive Diseases, vol. 28, 2010, pp. 220-224 (5 pages).

Yoshidome et al., "Secretion of Gastric Inhibitory Polypeptide in Patients with Bile Duct Obstruction," Scand J Gastroenterol, Jun. 1995, pp. 586-589 (4 pages).

* cited by examiner

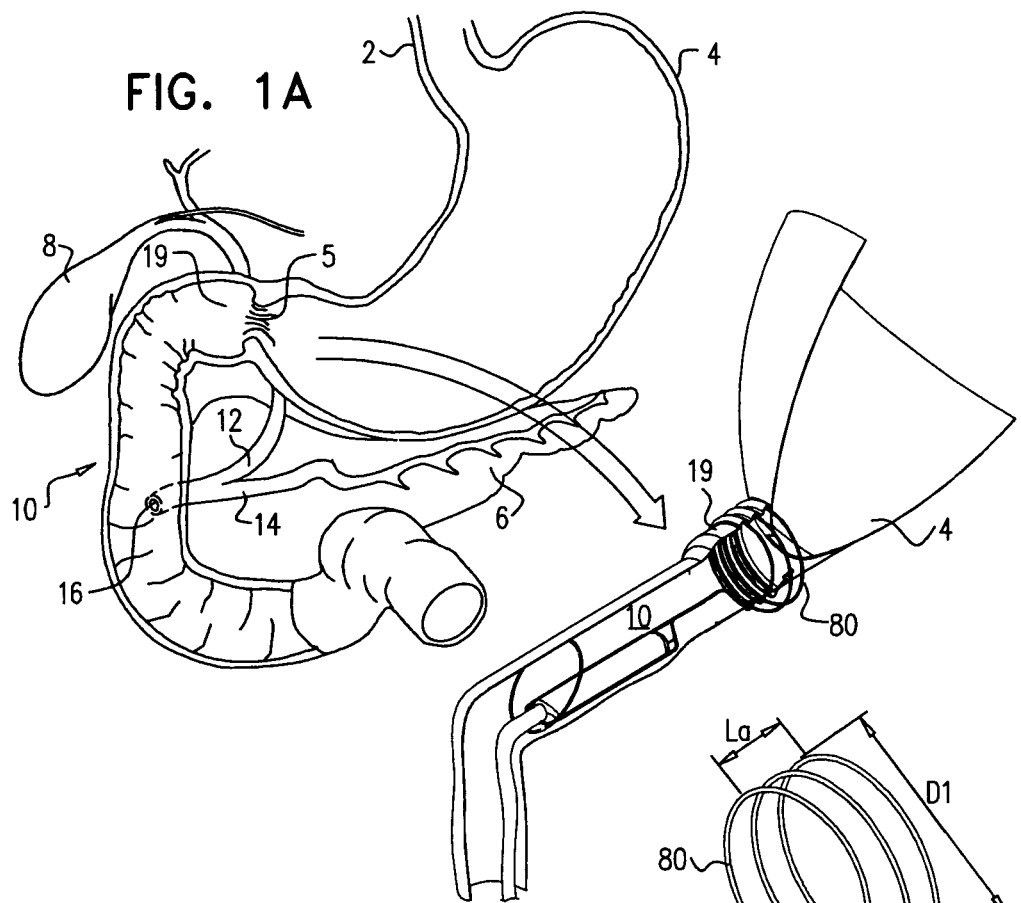
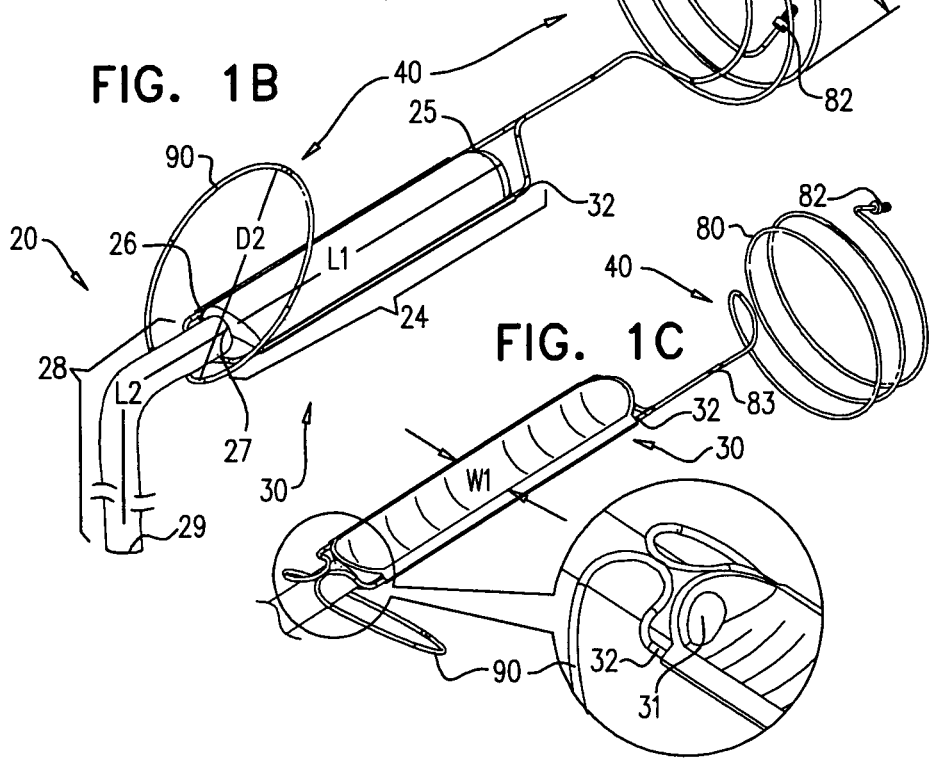
FIG. 1A
FIG. 1B
FIG. 1C

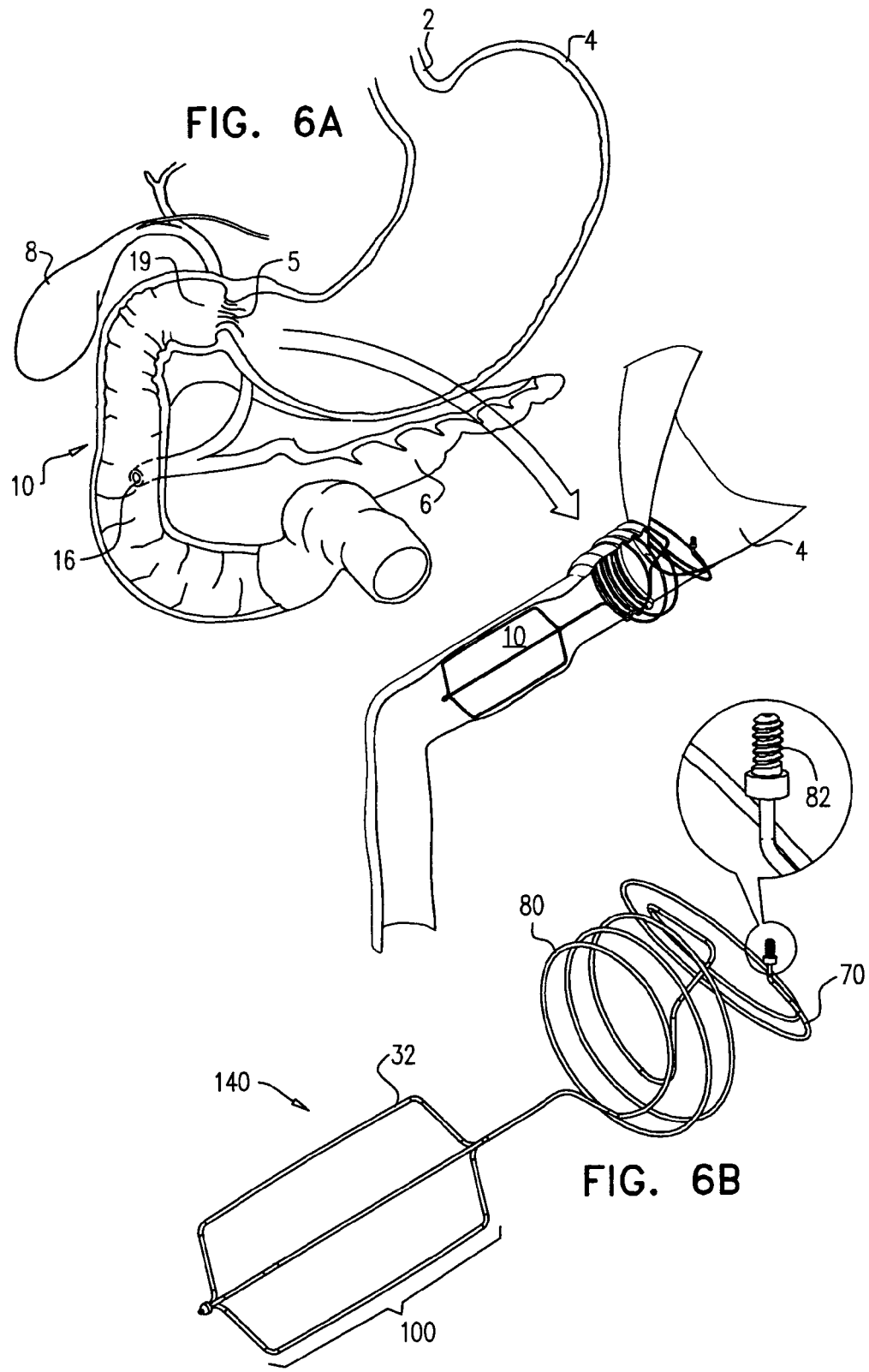

PANCREATICOBILIARY DIVERSION DEVICE

CROSS-REFERENCES TO RELATED APPLICATIONS

The present application is a U.S. national phase of PCT Application no. PCT/IL2011/000579 to Sharvit et al., filed Jul. 20, 2011, which published as WO 2012/011105to Sharvit et al., and which claims the priority of U.S. Provisional Application 61/366,586 to Sharvit et al., entitled, "Pancreatiobiliary diversion device," filed on Jul. 22, 2010, which is incorporated herein by reference.

FIELD OF THE APPLICATION

Embodiments of the present invention relate generally to treatment of obesity and other conditions, and particularly to treatment of obesity and other conditions by diversion of endogenous secretions.

BACKGROUND OF THE APPLICATION

The human gastrointestinal tract is a system by which ingested food is digested and absorbed in order to provide the body with essential nutrients. The human gastrointestinal tract includes the small intestine, which is the longest portion of the digestive tract. The small intestine has three sections: the duodenum, jejunum and ileum. The duodenum, where most chemical digestion takes place, precedes the jejunum and ileum and is the shortest part (typically 25-30 cm in length) of the small intestine. The duodenum begins with the duodenal bulb and ends at the ligament of Treitz.

The digestion process is regulated by several hormones, some of which are released by the gastrointestinal tract. Additionally, many digestive enzymes are secreted by the gastrointestinal tract and the pancreas to aid in the digestion of food. Other endogenous secretions, such as bile, facilitate the digestion of lipids in the small intestine. Bile is typically stored in the gallbladder and upon eating is discharged into the duodenum.

Obesity and type II diabetes are serious health concerns. It is believed that obesity promotes insulin resistance, and has been found to play an important role in the pathogenesis of diabetes. Accordingly, weight loss is generally recommended, in order to lower elevated blood glucose levels in overweight and obese individuals with type II diabetes.

Some weight loss surgical techniques currently include several types of bariatric surgical procedures, including malabsorptive procedures, e.g., biliopancreatic diversion and biliopancreatic diversion with a duodenal switch. Generally, these diversion procedures, although they also reduce stomach size, are based mainly on creating malabsorption by bypassing digestion in the duodenum and other parts of the small intestine.

SUMMARY OF APPLICATIONS

In some applications of the present invention, methods and apparatus are provided for diversion of pancreaticobiliary secretions from an anatomical entry location into a gastrointestinal tract to a location in the gastrointestinal tract that is distal to the anatomical entry location. Typically, bile and pancreatic secretions (i.e., pancreaticobiliary secretions) pass through the common bile duct and enter the duodenum at the major duodenal papilla. Some applications of the present invention comprise transferring the pancreaticobiliary secretions from the entry location e.g., at the duodenal papilla, to a location which is beyond the duodenum, e.g., beyond the ligament of Treitz which is the final section of the duodenum. In some applications, diversion of the pancreaticobiliary secretions substantially inhibits contact, in some sections of the small intestine, of the pancreaticobiliary secretions with ingested food passing within the gastrointestinal tract. Typically, inhibiting association of the pancreaticobiliary secretions with ingested food reduces emulsification and formation of micelles of ingested fat, and disrupts the process of fat digestion in the body.

For some applications, a pancreaticobiliary secretion-diversion guide that is configured for deployment within the gastrointestinal tract is provided. Typically, the pancreaticobiliary secretion-diversion guide is configured to collect the pancreaticobiliary secretions from the anatomical entry location, e.g., duodenal papilla, and deliver the pancreaticobiliary secretions to a location in the gastrointestinal tract that is distal to the duodenal papilla, e.g., beyond the duodenum (or at a more distal site within the duodenum).

In some applications, the pancreaticobiliary secretion-diversion guide has a proximal portion and a distal portion. In this context, in the specification and in the claims, "proximal" means closer to the orifice through which the guide is originally placed into the body, and "distal" means further from this orifice. For some applications, the proximal portion has a cross section that is larger than the cross section of the distal portion, in order to enable collecting of the pancreaticobiliary secretion into the guide lumen when the guide is positioned inside the gastrointestinal tract of a subject. Typically, the diversion guide is positioned in the gastrointestinal tract such that a section of the proximal portion of the guide is configured to collect at least 75% of the pancreaticobiliary secretions entering the duodenum, substantially without the diversion guide entering the duct through which the secretions pass, e.g., the common bile duct.

In some applications, the pancreaticobiliary secretion-diversion guide is shaped to define at least a portion of a tube comprising a tube wall having an inner surface and an outer surfaces, the tube wall inner surface defining a lumen for passage of partly-digested food (i.e., chyme) therethrough. Typically, the tube wall comprises an aperture portion. The aperture portion is shaped to define one or more apertures and contacts the wall of the gastrointestinal tract of the subject in order to provide contact between ingested food within the lumen and the wall of the gastrointestinal tract. The tube wall additionally comprises a channel portion, which collects pancreaticobiliary secretions from the anatomical entry location in the gastrointestinal tract, and inhibits contact of the pancreaticobiliary secretions with the food within the lumen.

Alternatively or additionally, an anchoring system is coupled to the pancreaticobiliary secretion-diversion guide, and is configured to maintain the pancreaticobiliary secretion-diversion guide in place within the gastrointestinal tract by generally applying pressure to a wall of the gastrointestinal tract. In some applications, the anchoring system comprises (a) one or more helical and/or ring anchors disposed upstream of the entry location of pancreaticobiliary secretions into the gastrointestinal tract (e.g., duodenal papilla) and (b) one or more helical and/or ring anchors disposed downstream of the entry location of the pancreaticobiliary secretions. Each of the above anchors is typically disposed entirely within the lumen of the gastrointestinal tract, and does not penetrate tissue of the gastrointestinal tract. For example, in order to inhibit penetration of tissue, the anchors may have rounded tips. The upstream anchors may be disposed within the stomach or within the duodenal bulb.

Particular applications of the pancreaticobiliary secretion-diversion guide and of the anchoring system are described herein.

There is therefore provided, in accordance with an application of the present invention, apparatus for use with pancreaticobiliary secretions that enter a gastrointestinal tract of a subject at an anatomical entry location, the apparatus including:

a pancreaticobiliary secretion-diversion guide configured to collect the pancreaticobiliary secretions from the anatomical entry location and deliver the pancreaticobiliary secretions to a location in the gastrointestinal tract that is distal to the anatomical entry location; and an anchoring system including one or more helical anchors located within the gastrointestinal tract and configured to apply pressure to a wall of the gastrointestinal tract in order to maintain the pancreaticobiliary secretion-diversion guide in place.

For some applications, the anatomical entry location includes a duodenal papilla of the subject, and the pancreaticobiliary secretion-diversion guide is configured to collect the pancreaticobiliary secretions that are secreted from the duodenal papilla.

For some applications, the pancreaticobiliary secretion-diversion guide is configured to collect the pancreaticobiliary secretions that are secreted from the duodenal papilla without entering a duct through which the secretions pass.

For some applications, the pancreaticobiliary secretion-diversion guide is configured to deliver the pancreaticobiliary secretions to a location that is beyond a ligament of Treitz of the subject.

For some applications, the pancreaticobiliary secretion-diversion guide is configured to deliver the pancreaticobiliary secretions to a location in the gastrointestinal tract that is 40-80 cm beyond the ligament of Treitz.

For some applications, the pancreaticobiliary secretion-diversion guide is configured to prevent the pancreaticobiliary secretions from contacting chyme in some portions of the gastrointestinal tract.

For some applications, the pancreaticobiliary secretion-diversion guide includes a proximal portion thereof and a distal portion thereof, the proximal portion having an area for collecting the secretions that is large enough to cover a five diameter hole.

For some applications, the pancreaticobiliary secretion-diversion guide includes a proximal end at a proximal portion thereof and a distal end at a distal portion thereof, the proximal portion having a cross section of 10-100 mm2, 10 mm from the proximal end, the distal portion having a cross section of 5-100 mm2, 10 mm from the distal end, the cross section of the proximal portion being at least two times greater than the cross section of the distal portion.

For some applications, the proximal portion has a length of 1-6 cm extending from the proximal end to a distal end thereof.

For some applications, the proximal portion has a width of 5-25 mm.

For some applications, the proximal portion has a width of 10-15 mm.

For some applications, the distal portion has a length of 50-110 cm extending from a proximal end thereof to the distal end thereof.

For some applications, the proximal portion is configured to collect at least 75% of the pancreaticobiliary secretions that are secreted into the gastrointestinal tract.

For some applications, the one or more helical anchors are configured to be disposed entirely within the lumen of the gastrointestinal tract, and not to penetrate tissue of the gastrointestinal tract.

For some applications, the anchoring system includes tissue-penetrating anchors configured to penetrate tissue of the gastrointestinal tract in order to maintain the pancreaticobiliary secretion-diversion guide in place.

For some applications, the one or more helical anchors are flexible.

For some applications, the one or more helical anchors each have a diameter of 20-35 mm when unconstrained.

For some applications, the one or more helical anchors are configured to be located upstream of the anatomical entry location of the pancreaticobiliary secretions.

For some applications, the one or more helical anchors are configured to be located within a duodenal bulb of the subject.

For some applications, the one or more helical anchors each have a diameter of 50-60 mm when located within the duodenal bulb.

For some applications, the one or more helical anchors each have a length of 2-40 mm, when unconstrained, measured along a longitudinal axis of each helical anchor.

For some applications, the one or more helical anchors each have a length of 5-15 mm, when unconstrained, measured along a longitudinal axis of each helical anchor.

For some applications, the one or more helical anchors are configured to be located downstream of the anatomical entry location of the pancreaticobiliary secretions.

For some applications, the pancreaticobiliary secretion-diversion guide is arranged to provide an entry point of the pancreaticobiliary secretions into the pancreaticobiliary secretion-diversion guide that is disposed between one of the one or more helical anchors and another one of the one or more helical anchors.

For some applications, the apparatus includes one or more ring anchors located within the gastrointestinal tract and configured to apply pressure to the wall of the gastrointestinal tract in order to maintain the pancreaticobiliary secretion-diversion guide in place.

For some applications, a silicone sheath is configured to surround at least a portion of the anchoring system and to apply pressure to the wall of the gastrointestinal tract in order to maintain the pancreaticobiliary secretion-diversion guide in place.

For some applications, the one or more ring anchors are configured to be disposed entirely within the lumen of the gastrointestinal tract, and not to penetrate tissue of the gastrointestinal tract.

For some applications, the ring anchor is configured to be located downstream of the anatomical entry location of the pancreaticobiliary secretions.

For some applications, the one or more ring anchors are flexible.

For some applications, the one or more ring anchors each have a diameter of 20-35 mm.

For some applications, the one or more ring anchors are configured to be positioned at a non-perpendicular angle with respect to a longitudinal axis of the pancreaticobiliary secretion-diversion guide.

For some applications, the apparatus includes an intragastric anchor configured to be located in a pyloric antrum of a stomach of the subject and configured to apply pressure to a wall of the stomach in order to maintain the pancreaticobiliary secretion-diversion guide in place.

For some applications, the intragastric anchor includes a helical anchor.

For some applications, the intragastric anchor has a longest dimension of 35-55 mm.

For some applications, the apparatus includes a retrieval element fixedly coupled to the anchoring system, configured for facilitating endoscopic retrieval of the apparatus.

For some applications, the apparatus includes at least one anchoring mount configured to be located in the gastrointestinal tract, downstream of the one or more helical anchors, the anchoring mount including two or more longitudinal struts.

For some applications, the anchoring mount is configured to be disposed entirely within the lumen of the gastrointestinal tract, and not to penetrate tissue of the gastrointestinal tract.

For some applications, at least one of the two or more longitudinal struts is configured to be aligned in parallel with a longitudinal axis of the gastrointestinal tract and at least one of the two or more longitudinal struts is a curved strut which is configured to contact the wall of the gastrointestinal tract to apply pressure thereto.

There is further provided, in accordance with an application of the present invention, apparatus for use with pancreaticobiliary secretions that enter a gastrointestinal tract of a subject at an anatomical entry location, the apparatus including:

a pancreaticobiliary secretion-diversion guide shaped to define a pancreaticobiliary secretion-diversion guide lumen having a proximal end at a proximal portion thereof and a distal end at a distal portion thereof, the proximal portion having a cross section of 10-100 mm2, 10 mm from the proximal end, the distal portion having a cross section of 5-100 mm2, 10 mm from the distal end, the cross section of the proximal portion being at least two times greater than the cross section of the distal portion; and an anchoring system configured to be located within the gastrointestinal tract and to apply pressure to a wall of the gastrointestinal tract in order to maintain the pancreaticobiliary secretion-diversion guide in place, the proximal portion of the pancreaticobiliary secretion-diversion guide is configured to collect pancreaticobiliary secretions from the anatomical entry location and the distal end of the pancreaticobiliary secretion-diversion guide is configured to deliver the pancreaticobiliary secretions to a location in the gastrointestinal tract that is distal to the anatomical entry location.

For some applications, the proximal portion is configured to collect at least 75% of the pancreaticobiliary secretions that are secreted into the gastrointestinal tract.

For some applications, the proximal portion has a length of 1-6 cm extending from the proximal end to a distal end thereof.

For some applications, the proximal portion has a width of 5-25 mm.

For some applications, the proximal portion has a width of 10-15 mm.

For some applications, the distal portion has a length of 50-110 cm extending from a proximal end thereof to the distal end thereof.

For some applications, the distal end is configured to deliver the pancreaticobiliary secretions to a location in the gastrointestinal tract that is 40-80 cm beyond a ligament of Treitz of the subject.

There is still further provided, in accordance with an application of the present invention, apparatus for use with pancreaticobiliary secretions that enter a gastrointestinal tract of a subject at an anatomical entry location, the apparatus including:

a pancreaticobiliary secretion-diversion guide configured to collect pancreaticobiliary secretions from the anatomical entry location and deliver the pancreaticobiliary secretions to a location in the gastrointestinal tract that is distal to the anatomical entry location; and an anchoring system configured to apply pressure to a wall of the gastrointestinal tract in order to maintain the pancreaticobiliary secretion-diversion guide in place, the anchoring system including:
one or more helical anchors configured to be disposed upstream of the entry location of pancreaticobiliary secretions into the gastrointestinal tract; and
one or more ring anchors configured to be disposed downstream of the entry location of the pancreaticobiliary secretions.

For some applications, the one or more helical anchors each have a diameter of 20-35 mm when unconstrained.

For some applications, the one or more helical anchors are configured to be located within a duodenal bulb of the subject.

For some applications, the one or more helical anchors each have a diameter of 50-60 mm when located within the duodenal bulb.

For some applications, the one or more helical anchors each have a length of 2-40 mm, when unconstrained, measured along a longitudinal axis of each helical anchor.

For some applications, the one or more helical anchors each have a length of 5-15 mm, when unconstrained, measured along a longitudinal axis of each helical anchor.

For some applications, the one or more helical anchors are flexible.

For some applications, the one or more ring anchors are flexible.

For some applications, the one or more ring anchors each have a diameter of 20-35 mm when unconstrained.

For some applications, the one or more ring anchors are configured to be positioned at a non-perpendicular angle with respect to a longitudinal axis of the pancreaticobiliary secretion-diversion guide.

For some applications, the apparatus includes an intragastric anchor configured to be located in a lumen of a pyloric antrum of a stomach of the subject and configured to apply pressure to a wall of the stomach in order to maintain the pancreaticobiliary secretion-diversion guide in place.

For some applications, the intragastric anchor includes a helical anchor.

For some applications, the pancreaticobiliary secretion-diversion guide is arranged to provide an entry point of the pancreaticobiliary secretions into the pancreaticobiliary secretion-diversion guide which is disposed between one of the one or more helical anchors and one of the one or more ring anchors.

For some applications, the one or more helical anchors and the one or more ring anchors are configured to be disposed entirely within the lumen of the gastrointestinal tract, and not to penetrate tissue of the gastrointestinal tract.

There is additionally provided, in accordance with an application of the present invention, apparatus for use with pancreaticobiliary secretions that enter a gastrointestinal tract of a subject at an anatomical entry location, the apparatus including:

a pancreaticobiliary secretion-diversion guide configured to collect pancreaticobiliary secretions from the anatomical entry and deliver the pancreaticobiliary secretions to a location in the gastrointestinal tract that is distal to the anatomical entry location; and an anchoring system configured to apply pressure to a wall of the gastrointestinal tract in order to maintain the pancreaticobiliary secretion-diversion guide in place, the anchoring system including:
one or more helical anchors configured to be disposed upstream of the entry location of pancreaticobiliary secretions into the gastrointestinal tract; and
one or more helical anchors configured to be disposed downstream of the entry location of pancreaticobiliary secretions into the gastrointestinal tract.

For some applications, the one or more helical anchors each have a diameter of 20-35 mm when unconstrained.

For some applications, the one or more helical anchors configured to be disposed upstream of the entry location of pancreaticobiliary secretions into the gastrointestinal tract, are configured to be located within a duodenal bulb of the subject.

For some applications, the one or more helical anchors each have a diameter of 50-60 mm when located within the duodenal bulb.

For some applications, the one or more helical anchors each have a length of 2-40 mm, when unconstrained, measured along a longitudinal axis of each helical anchor.

For some applications, the one or more helical anchors each have a length of 5-15 mm, when unconstrained, measured along a longitudinal axis of each helical anchor.

For some applications, the one or more helical anchors are flexible.

For some applications, the one or more helical anchors are configured to be positioned at a non-perpendicular angle with respect to a longitudinal axis of the pancreaticobiliary secretion-diversion guide.

For some applications, the apparatus includes an intragastric anchor configured to be located in a pyloric antrum of a stomach of the subject and configured to apply pressure to a wall of the stomach in order to maintain the pancreaticobiliary secretion-diversion guide in place.

For some applications, the intragastric anchor includes a helical anchor.

For some applications, the pancreaticobiliary secretion-diversion guide is arranged to provide an entry point of the pancreaticobiliary secretions into the pancreaticobiliary secretion-diversion guide that is disposed between one of the one or more helical anchors configured to be disposed upstream of the entry location of the pancreaticobiliary secretions, and one of the one or more helical anchors configured to be disposed downstream of the entry location of the pancreaticobiliary secretions.

For some applications, the one or more helical anchors are configured to be disposed entirely within the lumen of the gastrointestinal tract, and not to penetrate tissue of the gastrointestinal tract.

There is yet additionally provided, in accordance with an application of the present invention, apparatus for use with pancreaticobiliary secretions that enter a gastrointestinal tract of a subject at an anatomical entry location, the apparatus including:
a pancreaticobiliary secretion-diversion guide configured to collect pancreaticobiliary secretions from the anatomical entry location and deliver the pancreaticobiliary secretions to a location in the gastrointestinal tract that is distal to the anatomical entry location;
an anchoring system configured to apply pressure to a wall of the gastrointestinal tract in order to maintain the pancreaticobiliary secretion-diversion guide in place including:
one or more helical anchors configured to be located upstream of the entry location of pancreaticobiliary secretions into the gastrointestinal tract; and
at least one anchoring mount configured to be located in the gastrointestinal tract, downstream of the one or more helical anchors, the anchoring mount including two or more longitudinal struts, configured to be aligned in parallel with a longitudinal axis of the gastrointestinal tract.

For some applications, the one or more helical anchors and the at least one anchoring mount are configured to be disposed entirely within the lumen of the gastrointestinal tract, and not to penetrate tissue of the gastrointestinal tract.

There is still additionally provided, in accordance with an application of the present invention, apparatus for use with pancreaticobiliary secretions that enter a gastrointestinal tract of a subject at an anatomical entry location, the apparatus including:
a pancreaticobiliary secretion-diversion guide shaped to define at least a portion of a tube, the tube including a tube wall, the tube wall having an inner surface and an outer surface, the tube wall inner surface defining a lumen for passage of food therethrough,
the tube wall includes:
an aperture portion, shaped to define one or more apertures and configured to contact a wall of a gastrointestinal tract of a subject and to provide contact between food within the lumen and the wall of the gastrointestinal tract; and
a channel portion, configured to collect pancreaticobiliary secretions from the anatomical entry location, and to inhibit contact of the pancreaticobiliary secretions with the food within the lumen.

For some applications, the one or more apertures include between 1-5 apertures.

For some applications, the one or more apertures include between 5-50 apertures.

For some applications, each of the one or more apertures has a cross sectional area of at least 1 cm2.

For some applications, the one or more apertures are configured to provide contact between chyme within the lumen of the tube wall inner surface and the wall of the gastrointestinal tract.

For some applications, the pancreaticobiliary secretion-diversion guide has a length of 60-110 cm.

For some applications, the tube wall inner surface lumen has a diameter of 20-35 mm.

There is further additionally provided, in accordance with an application of the present invention, apparatus for use with pancreaticobiliary secretions that enter a gastrointestinal tract of a subject at an anatomical entry location, the apparatus including:
a pancreaticobiliary secretion-diversion guide configured to transfer pancreaticobiliary secretions from the anatomical entry location to a location in the gastrointestinal tract that is distal to the anatomical entry location; and
one or more arms, coupled to the guide, and configured to apply pressure to the wall of the gastrointestinal tract in order to maintain the pancreaticobiliary secretion-diversion guide in place in the gastrointestinal tract.

For some applications, the pancreaticobiliary secretion-diversion guide is shaped to define a channel in fluid communication with the wall of the gastrointestinal tract when the guide is in the gastrointestinal tract.

For some applications, the pancreaticobiliary secretion-diversion guide is configured to inhibit contact in some sections of the gastrointestinal tract between the pancreaticobiliary secretions and chyme passing through the gastrointestinal tract.

For some applications, the pancreaticobiliary secretion-diversion guide has a length of 60-110 cm.

For some applications, the pancreaticobiliary secretion-diversion guide is configured to deliver the pancreaticobiliary secretions to a location in the gastrointestinal tract that is 40-80 cm beyond the ligament of Treitz.

There is yet additionally provided, in accordance with an application of the present invention, apparatus for use with pancreaticobiliary secretions that enter a gastrointestinal tract of a subject at an anatomical entry location, the apparatus including:

a pancreaticobiliary secretion-diversion guide shaped to define at least a portion of a tube, the tube including a tube wall, the tube wall having an inner surface and an outer surface, the tube wall inner surface defining a lumen for passage of food therethrough, the tube wall includes:

an aperture portion, shaped to define one or more apertures and configured to contact a wall of a gastrointestinal tract of a subject and to provide contact via the apertures between food within the lumen and the wall of the gastrointestinal tract; and an inner tube shaped to define a lumen coupled to the inner surface of the tube wall, configured to transfer pancreaticobiliary secretions from the anatomical entry location to a location in the gastrointestinal tract that is distal to the anatomical entry location.

For some applications, the lumen of the tube wall inner surface has a diameter of 20-35 mm.

For some applications, the pancreaticobiliary secretion-diversion guide has a length of 60-110 cm.

For some applications, the one or more apertures include between 1-5 apertures.

For some applications, the one or more apertures include between 5-50 apertures.

For some applications, each of the one or more apertures has a cross sectional area of at least 1 cm2.

For some applications, the inner tube is shaped to define an orifice, in a lateral wall of the lumen, having a diameter of 5-20 mm.

For some applications, the inner tube has a length of 60-110 cm.

There is yet further provided, in accordance with an application of the present invention, a method, including:

deploying within a gastrointestinal tract a pancreaticobiliary secretion-diversion guide configured to collect pancreaticobiliary secretions from an anatomical entry location and deliver the pancreaticobiliary secretions to a location in the gastrointestinal tract that is distal to the anatomical entry location; and implanting an intragastric anchor, coupled to the guide, in a pyloric antrum of a stomach of a subject, the anchor configured to apply pressure to a wall of the stomach in order to maintain the guide in place.

For some applications, the method includes implanting in a small intestine of the subject an anchoring system coupled to the guide, the anchoring system including one or more anchors configured to apply pressure to a wall of the gastrointestinal tract in order to maintain the guide in place.

The present invention will be more fully understood from the following detailed description of embodiments thereof, taken together with the drawings, in which:

BRIEF DESCRIPTION OF THE DRAWINGS

FIGS. 1A-C are schematic illustrations of apparatus for diversion of pancreaticobiliary secretions, in accordance with some applications of the present invention;

FIGS. 6A-B are schematic illustrations of an alternative configuration of the anchoring system for use with a pancreaticobiliary secretion-diversion guide as shown in FIGS. 5A-B, in accordance with an application of the present invention;

DETAILED DESCRIPTION OF APPLICATIONS

Figure 2A:
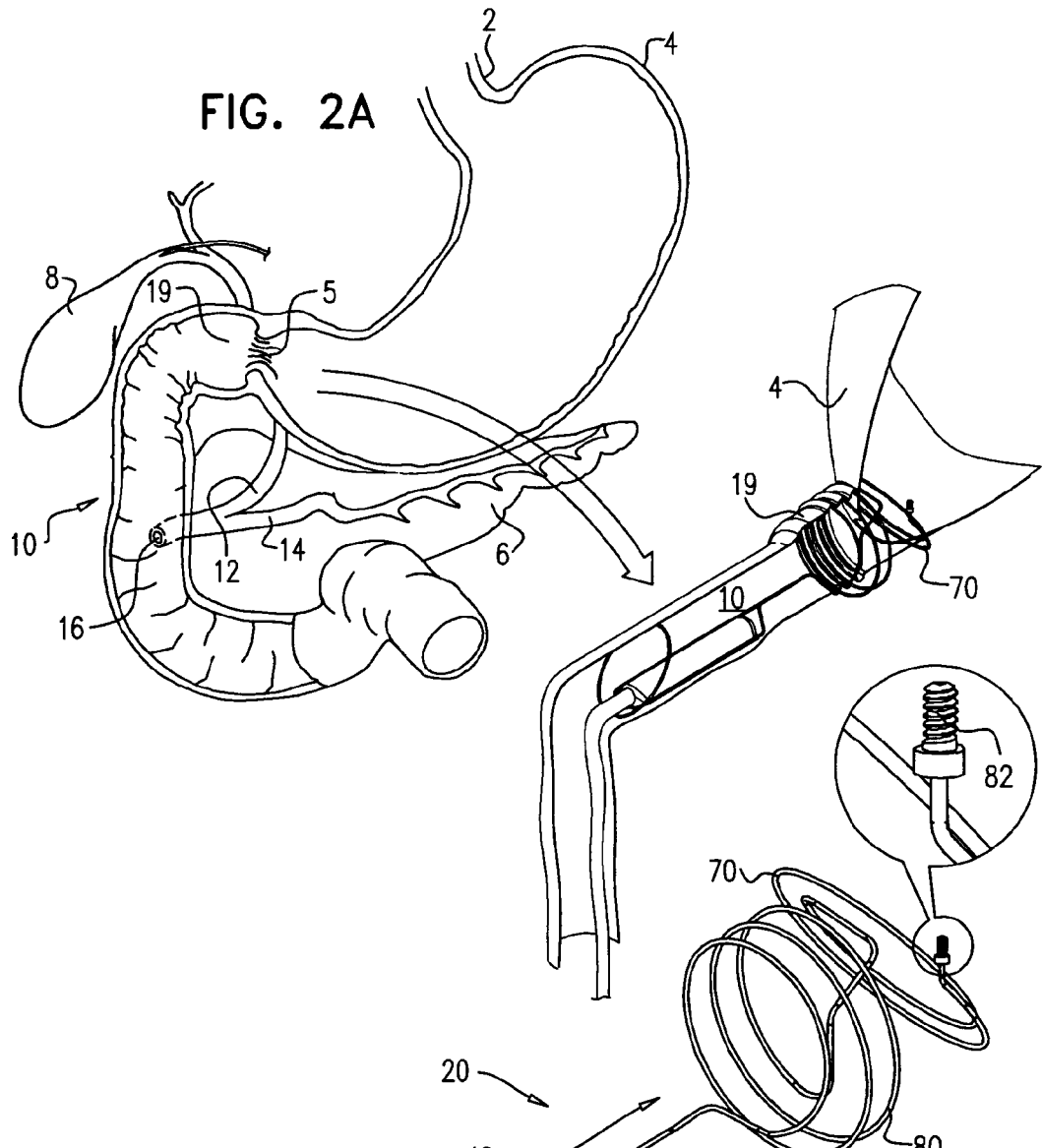
FIGS. 2A-B are schematic illustrations of an alternative configuration of the anchoring system of the apparatus shown in FIGS. 1A-B, in accordance with some applications of the present invention.

Reference is made to FIGS. 1A-B, which are schematic illustrations of apparatus 20 for diversion of pancreaticobiliary secretions, in accordance with some applications of the present invention. Apparatus 20 is typically configured for placement inside a gastrointestinal tract of a subject. FIG. 1A provides a schematic illustration of several components of a human digestive system. During the process of food digestion, food passes through esophagus 2 into stomach 4. The content of stomach 4 passes through pylorus 5 into the first section of the small intestine, duodenum 10. Bile, which aids in the process of fat digestion, is stored between meals in gallbladder 8. When the bile is released from gallbladder 8, it flows through the cystic duct and the common bile duct 12. Pancreas 6 produces exocrine secretions, including digestive enzymes, which pass through pancreatic duct 14. Pancreatic duct 14 merges with common bile duct 12 and together they form, at a medial side of a second portion of duodenum 10, a structure called the major duodenal papilla 16. Thus, major duodenal papilla 16, is an anatomical entry location of pancreaticobiliary secretions into the gastrointestinal tract. In some cases, common bile duct 12 discharges into the duodenum through a papilla which is in close proximity to major duodenal papilla 16. It will be appreciated that some applications of the present are applicable to such cases.

As shown in FIGS. 1A-C, some applications of the present invention comprise apparatus 20 comprising a pancreaticobiliary secretion-diversion guide 30 and anchoring system 40. Guide 30 is configured to collect pancreaticobiliary secretions from an anatomical entry location into duodenum 10, e.g., duodenal papilla 16, and deliver the pancreaticobiliary secretions to a location in the gastrointestinal tract that is distal to the duodenal papilla. For some applications, guide 30 transfers the pancreaticobiliary secretions to a location that is beyond the duodenum, e.g., beyond the ligament of Treitz, which is the final section of the duodenum. For some applications, guide 30 diverts the pancreaticobiliary secretions to a location that is at least 40 cm or less than 80 cm or between 40 and 80 cm beyond the ligament of Treitz. For some applications, guide 30 is configured to divert the pancreaticobiliary secretions to any location within the small intestine that is distal to the ligament of Treitz.

Guide 30 is inserted into a gastrointestinal tract of a subject. Guide 30 is typically disposed within duodenum 10 in a location that is in the vicinity of duodenal papilla 16, such that secretions entering the duodenum at papilla 16 are directly collected into guide 30. The pancreaticobiliary secretions flow through guide 30 and are typically discharged from the guide in an area that is in the upper and/or mid jejunum. It is to be noted that for some applications guide 30 is configured (i.e., sufficient in length) to deliver the pancreaticobiliary secretions to a location that is in the lower jejunum or the ileum of the small intestine.

Guide 30 generally prevents the pancreaticobiliary secretions from contacting at least a portion of the wall of the duodenum. Additionally, guide 30 is typically impermeable, thus isolating the pancreaticobiliary secretions and substantially inhibiting contact, in some sections of the small intestine, between the pancreaticobiliary secretions and partly digested food passing within the gastrointestinal tract (generally referred to as "chyme"). Typically, inhibiting contact of the pancreaticobiliary secretions with chyme reduces emulsification and formation of micelles of ingested fat, and disrupts the process of fat digestion in the body.

Reference is made to FIG. 1B. Typically, pancreaticobiliary secretion-diversion guide 30 has a proximal portion 24 comprising a proximal end 25 and a distal end 26, and a distal portion 28, which is shaped to define a pancreaticobiliary secretion-diversion guide lumen, comprising a proximal end 27 and a distal end 29. Proximal portion 24 typically has a length L1 of at least 1 cm or less than 6 cm or between 1 cm and 6 cm that extends from proximal end 25 to distal end 26. Proximal portion 24 typically has a width W of at least 5 mm (e.g., at least 10 mm) or less than 25 mm (e.g., less than 15 mm) or between 10 and 15 mm. Distal portion 28 typically has a length L2 of at least 50 cm or less than 110 cm or between 50 and 110 cm that extends from proximal end 27 to distal end 29. It is to be noted that proximal portion 24 is shown as having a generally semi-elliptical cross-section by way of illustration and not limitation. Proximal portion 24 may have any suitable shape, e.g., semi-circular.

FIGS. 1A-C show proximal portion 24 and distal portion 28 of guide 30 as discrete segments by way of illustration and not limitation. For other applications guide 30 may comprise a single component, e.g., a single hollow cylinder tube. Alternatively, proximal portion 24 and distal portion 28 of guide 30 are discrete segments having a smooth transition along the length of the tube.

Typically, as shown in FIG. 1C, proximal portion 24 has an open, generally, concave side, in order to enable collecting of the pancreaticobiliary secretions into the guide lumen when the guide is positioned inside the gastrointestinal tract of a subject. The open side of proximal portion 24 is typically configured to contact the wall of duodenum 10 in the vicinity of papilla 16 in order to collect pancreaticobiliary secretions into guide 30. Pancreaticobiliary secretions collected by proximal portion 24 flow to distal portion 28 through orifice 31, as shown in FIG. 1C. Distal portion 28 is open at distal end 29 thereof, allowing discharge of the pancreaticobiliary secretions.

For some applications, proximal portion 24 has a cross-sectional area of 10-100 mm2, 10 mm from proximal end 25. Distal portion 28 typically has a cross-sectional area of 5-100 mm2, 10 mm from distal end 29, the cross-sectional area of proximal portion 24 typically being at least two times greater than the cross-section area of the distal portion 28. Guide 30 is positioned in the gastrointestinal tract such that proximal portion 24 of guide 30 is configured to collect at least 75% of the pancreaticobiliary secretion entering the duodenum, substantially without guide 30 entering papilla 16 and/or a duct through which the secretions pass, e.g., common bile duct 12. Additionally, proximal portion 24 may enable collection of pancreaticobiliary secretions from additional entry points of pancreaticobiliary secretions into the duodenum in the vicinity of major duodenal papilla 16. The area of proximal portion 24 that is open to the duodenal papilla, in order to receive the secretions, is typically large enough to completely cover the papilla, e.g., large enough to cover a hole (the papilla) which has a diameter of 5 mm. As shown in FIG. 1C, the opening is considerably larger than this minimum size, and is typically at least 1 cm2, e.g., at least 2 cm2, and/or is less than 20 cm2, e.g., less than 12 cm2.

For other applications, guide 30 is shaped to define a tube having a tube wall configured for passage of pancreaticobiliary secretions therethrough. Typically, at least a portion of the tube contacts the wall of duodenum 10 in the vicinity of entry locations of pancreaticobiliary secretions into duodenum 10, e.g., papilla 16. For some applications, the tube is shaped to define a wide, funnel, proximal portion configured to contact the wall of duodenum 10 in the vicinity of papilla 16 in order to collect pancreaticobiliary secretions into the tube. For such applications, the tube may become progressively smaller in cross-section towards a distal portion thereof. For such applications, the diameter of the proximal portion is at least 5 mm or less than 20 mm or between 5-20 mm, and is configured to surround at least the entire diameter of the duodenal papilla.

For some applications (not shown), the portion of guide 30 which comes in contact with the wall of duodenum 10 in the vicinity of papilla 16 is shaped to define one or more, e.g., 1-10 or 10-100 or 100-1000, apertures which allow pancreaticobiliary secretions to enter guide 30. For some applications, the apertures are 2-5 mm in diameter.

Apparatus 20 comprises anchoring system 40, which is coupled to pancreaticobiliary secretion-diversion guide 30 and functions to maintain guide 30 in place within the intestine, even while the intestine undergoes peristalsis. For some applications, anchoring system 40 comprise one or more anchors located within the gastrointestinal tract and configured to apply pressure to a wall of the gastrointestinal tract in order to maintain pancreaticobiliary secretion-diversion guide 30 in place.

For some applications, anchoring system 40 comprises one or more helical anchors disposed upstream of the entry location of pancreaticobiliary secretions into the gastrointestinal tract and one or more ring anchors disposed downstream of the entry location of the pancreaticobiliary secretions. As shown in FIGS. 1A-C, anchoring system 40 comprises helical anchor 80, which is disposed upstream of the entry location of pancreaticobiliary secretions into the gastrointestinal tract, i.e., upstream of duodenal papilla 16. Anchor 80 is shown as comprising three helical turns by way of illustration and not limitation. Anchor 80 may comprise any suitable number of helical turns. Anchor 80 is shaped to define an anchor lumen which allows passage of chyme therethrough. Anchor 80 typically assumes a diameter D1 of 50-60 mm when deployed within the gastrointestinal tract. A resting diameter D1 of anchor 80 (i.e., if not constrained by the gastrointestinal tract) is typically at least 20 mm, or less than 35 mm, or between 20-35 mm. A resting length $L_a$ of anchor 80 (i.e., if not constrained by the gastrointestinal tract) is typically 2-40 mm, e.g., 5-15 mm, measured along a longitudinal axis of each helical anchor. It is to be noted that the pitch, i.e., the distance between turns of the helical anchor, may vary from one turn to the next. For some applications, anchor 80 comprises a flexible anchor. Typically, the flexibility of anchor 80 facilitates endoscopic passage of anchor 80 in a generally compressed state thereof through the esophagus.

FIG. 1A shows anchor 80 deployed within the first section of duodenum 10, duodenal bulb 19. Anchor 80 pushes against the walls of duodenal bulb 19, and applies pressure to the wall of duodenal bulb 19 in order to fix pancreaticobiliary secretion-diversion guide 30 in place. Anchor 80 typically comprises retrieval element 82 allowing safe retrieval of anchoring system 40 from within the body of the subject.

For some applications, an extension 83 from anchor 80 leads to one or more (e.g., two) longitudinal struts 32 which are coupled to proximal portion 24 of pancreaticobiliary secretion-diversion guide 30, to fix guide 30 within the intestine.

In some applications, anchoring system 40 additionally comprises one or more ring anchors 90 configured to be disposed downstream of the entry location of pancreaticobiliary secretions into the gastrointestinal tract, e.g., downstream of duodenal papilla 16. For some applications, ring anchor 90 comprises a flexible, elastic anchor, which applies an outward force to the intestine. Typically, the flexibility of anchor 90 facilitates endoscopic passage of anchor 90 through the esophagus in a highly elliptical shape. When anchor 90 is deployed within the intestine, it naturally relaxes to assume a less elliptical shape (i.e., more circular), applying a force to the intestine wall. Ring anchor 90 typically surrounds a portion of pancreaticobiliary secretion-diversion guide 30. FIGS. 1A-B show ring anchor 90 surrounding a portion of distal portion 28 of guide 30 and leaning against proximal portion 24 in order to apply pressure thereto to maintain guide 30 in place. Anchor 90 may be positioned generally perpendicularly with respect to a longitudinal axis of guide 30, or as shown in FIGS. 1A-B, at a non-perpendicular angle with respect to a longitudinal axis of guide 30. Ring anchor 90 is shaped to define an anchor lumen which allows passage of chyme therethrough. Anchor 90 typically has a diameter D2 of 20-35 mm, e.g., 25-35 mm when not constrained.

Alternatively, for some applications, anchor 80 may be disposed between the duodenal bulb and the entry location of pancreaticobiliary secretions into the gastrointestinal tract. For such applications, D1 is generally the same as D2 when deployed within the gastrointestinal tract.

For some applications, anchor 90 is configured to be disposed upstream of the entry location of pancreaticobiliary secretions into the gastrointestinal tract, e.g., upstream of duodenal papilla 16, and anchor 80 is configured to be disposed downstream of the entry location of pancreaticobiliary secretions into the gastrointestinal tract, e.g., downstream of duodenal papilla 16.

Each of the above anchors is typically disposed entirely within the lumen of the gastrointestinal tract, and does not penetrate tissue of the gastrointestinal tract. For example, in order to inhibit penetration of tissue, the anchors may have rounded tips. The upstream anchors may be disposed within the stomach or within the duodenal bulb. Alternatively, the upstream anchors may be disposed between the duodenal bulb and the entry location of pancreaticobiliary secretions into the gastrointestinal tract.

Figure 2B:
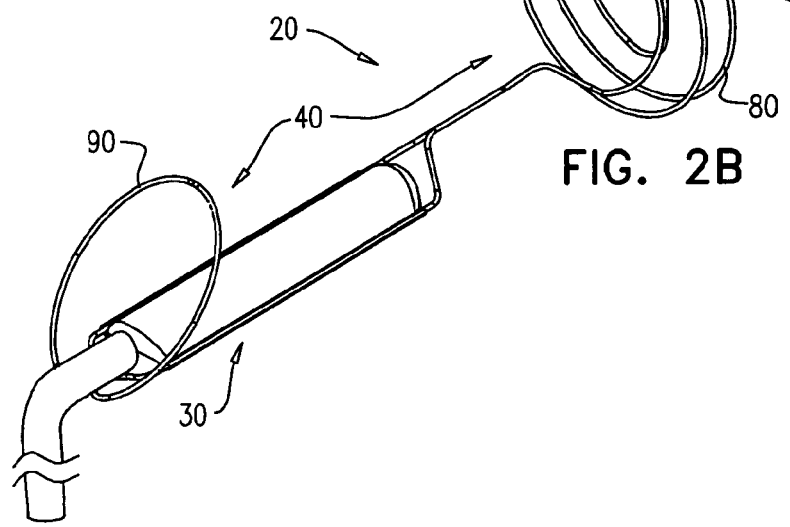

Reference is made to FIGS. 2A-B, which are schematic illustrations of an alternative configuration of the anchoring system of apparatus 20, in accordance with some applications of the present invention. For some applications, anchoring system 40 comprises an additional intragastric anchor 70, which is configured for deployment within a pyloric antrum of the stomach of the subject. Intragastric anchor 70 is coupled to helical anchor 80. Intragastric anchor 70 is shown having two helical turns by way of illustration and not limitation. Intragastric anchor 70 may comprise any suitable number of turns, or, alternatively, no turns. Typically, intragastric anchor 70 has a longest dimension of 35-55 mm. Intragastric anchor 70 typically contacts the wall of the stomach in order to apply pressure to the wall and maintain guide 30 in place.

Retrieval element 82 in this application is coupled to intragastric anchor 70. An exploded view of retrieval element 82 shows element 82 shaped to define a screw in order to facilitate deployment in the gastrointestinal tract, and retrieval of apparatus 20 or portions thereof. Alternatively, element 82 may define any other suitable shape.

Figure 3A:
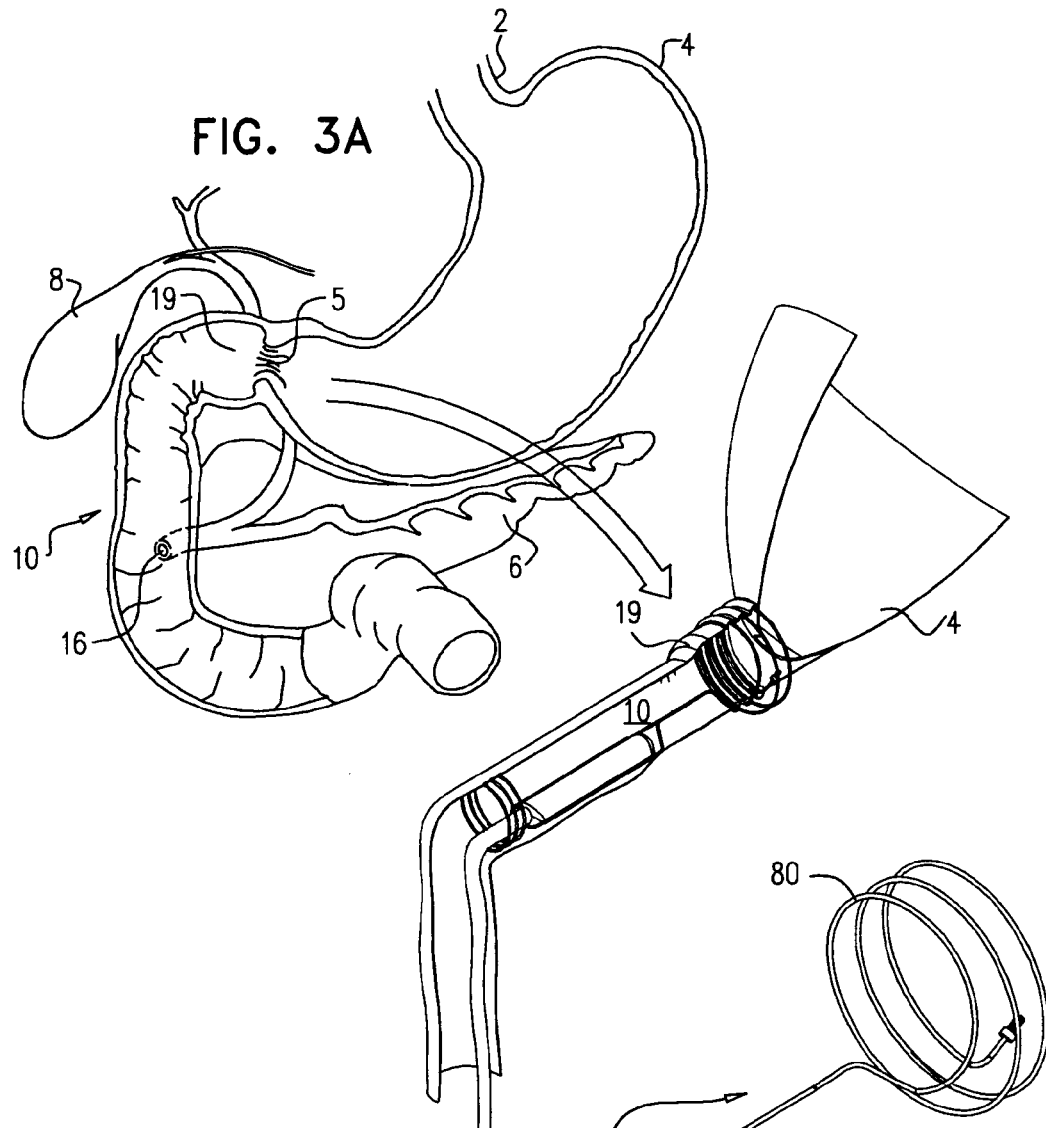
FIGS. 3A-B are schematic illustrations of another alternative configuration of the anchoring system, in accordance with some applications of the present invention.
Figure 3B:
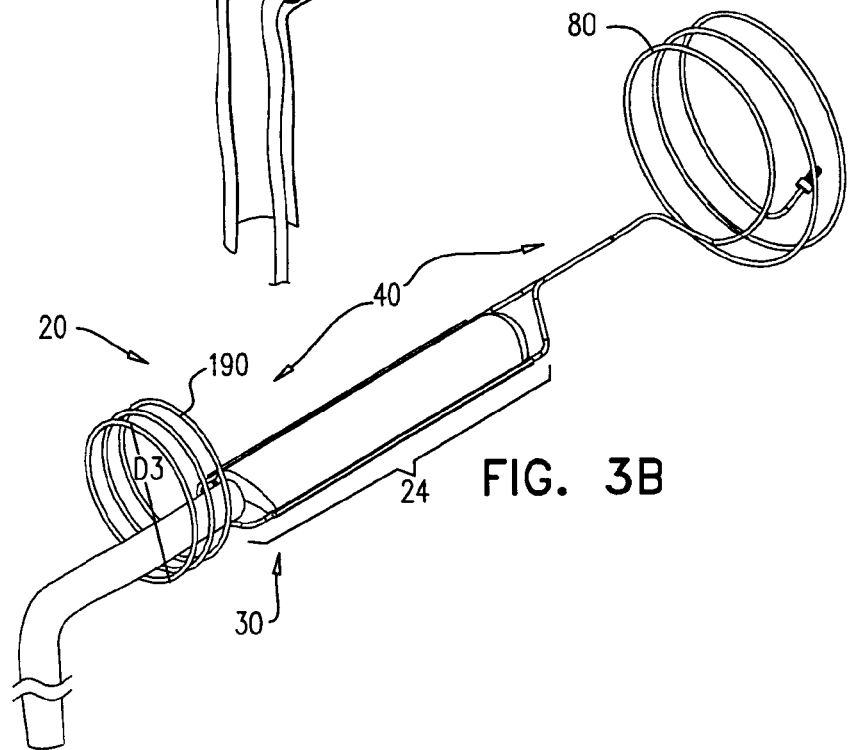

Reference is made to FIGS. 3A-B, which are schematic illustrations of another alternative configuration of the anchoring of the apparatus 20, in accordance with some applications of the present invention.

For some applications, anchoring system 40 comprises one or more helical anchors 190 which are disposed downstream of the entry location of pancreaticobiliary secretions into the gastrointestinal tract, e.g., downstream of duodenal papilla 16. Helical anchor 190 typically surrounds a portion of pancreaticobiliary secretion-diversion guide 30. FIGS. 3A-B show helical anchor 190 surrounding a portion of distal portion 28 of guide 30. Anchor 190 may be positioned generally perpendicularly with respect to a longitudinal axis of guide 30 as shown in FIGS. 3A-B, or at an angle with respect to a longitudinal axis of guide 30 (configuration not shown). Helical anchor 190 is shaped to define an anchor lumen which allows passage of chyme therethrough. Anchor 190 typically assumes a diameter D3 of 20-35 mm, e.g., 25-35 mm when unconstrained by the gastrointestinal tract. Helical anchor 190 is shown having three helical turns by way of illustration and not limitation. Anchor 190 may comprise any suitable number of helical turns. Helical anchor 190 typically contacts the wall of the intestine in order to apply pressure to the wall and maintain guide 30 in place.

Figure 4A:
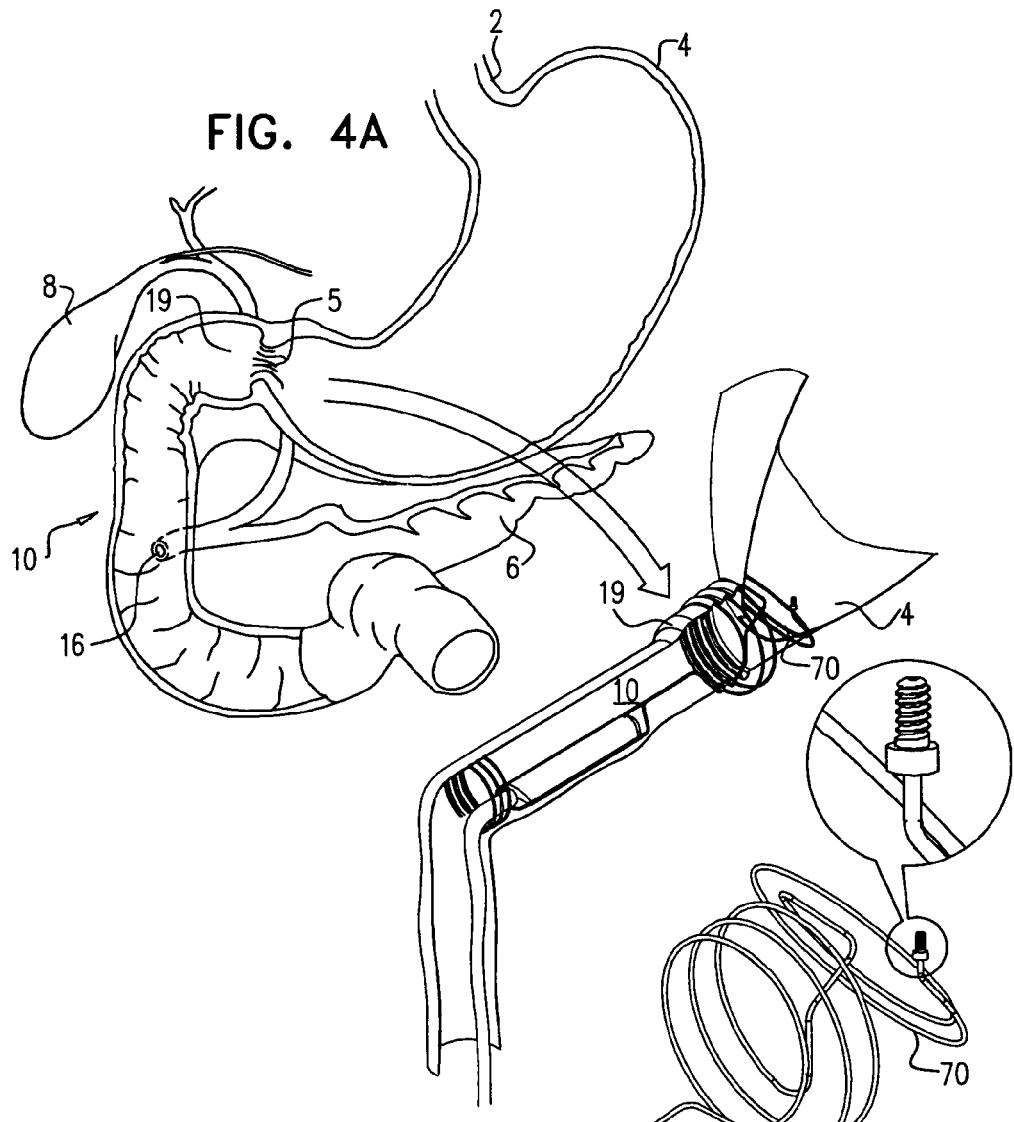
FIGS. 4A-B are schematic illustrations of an alternative configuration of the anchoring system of the apparatus shown in FIGS. 3A-B, in accordance with some applications of the present invention.
Figure 4B:
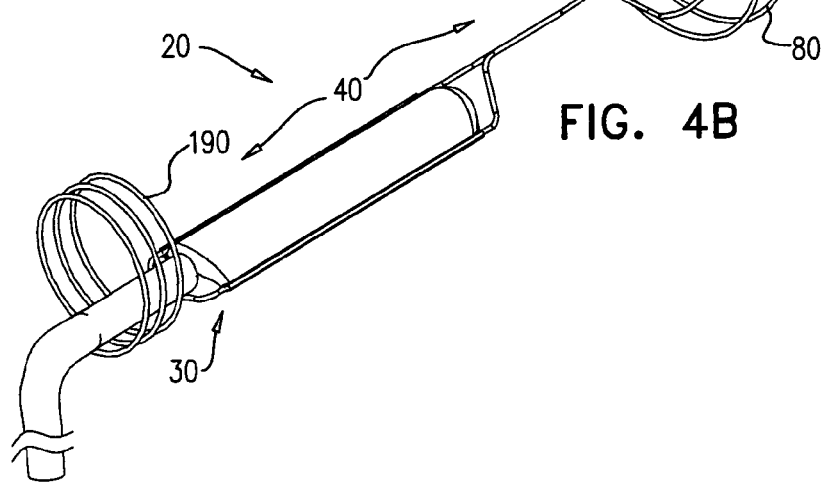

Reference is made to FIGS. 4A-B which are schematic illustrations of an alternative configuration of the anchoring system of apparatus 20, in accordance with some applications of the present invention. For some applications, anchoring system 40 comprises anchor 190 and an additional intragastric anchor 70 which is configured for deployment within the pyloric antrum of stomach 4 of the subject as described with reference to FIG. 2A-B.

Figure 5A:
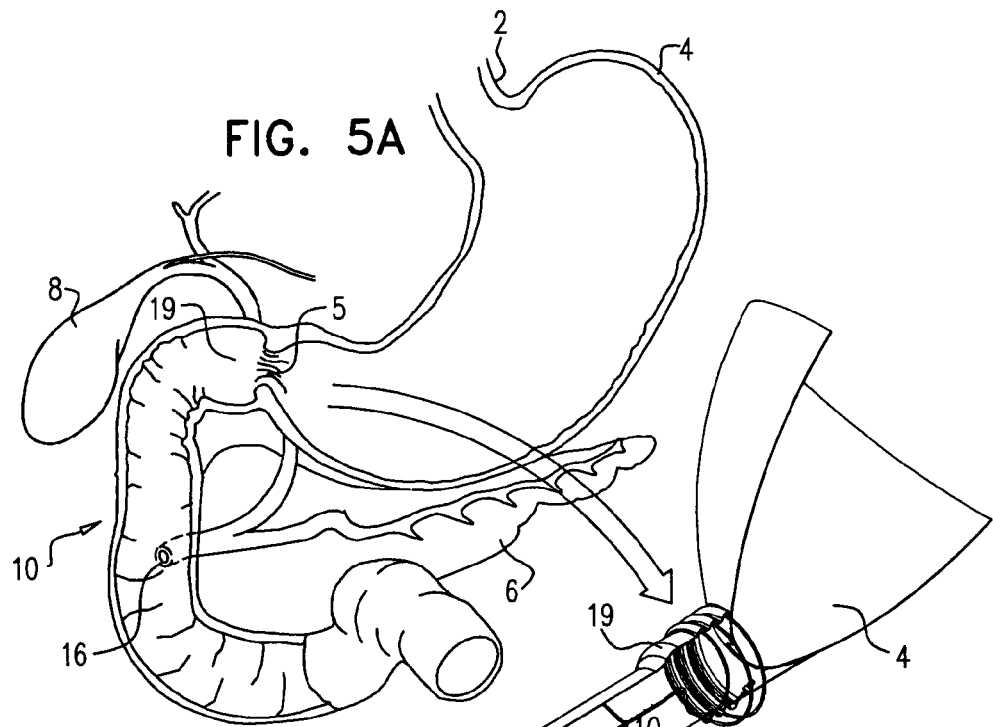
FIGS. 5A-B are schematic illustrations of an anchoring system for use with a pancreaticobiliary secretion-diversion guide, in accordance with some applications of the present invention.
Figure 5B:
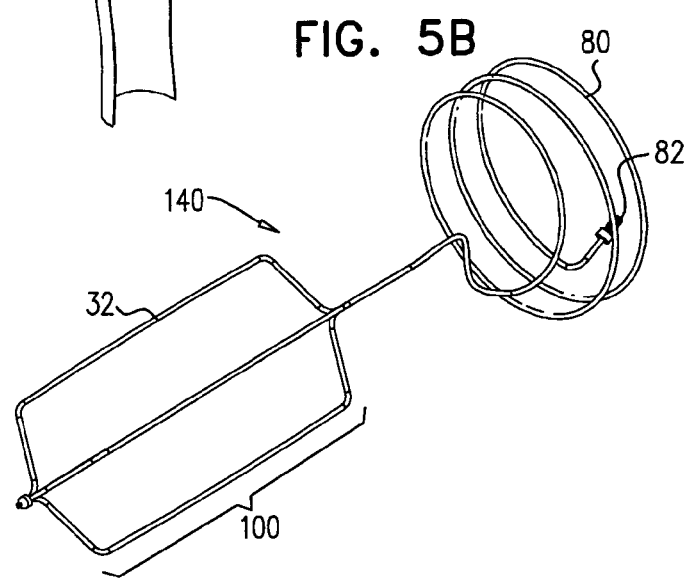

Reference is made to FIGS. 5A-B, which are schematic illustrations of anchoring system 140 for use with a pancreaticobiliary secretion-diversion guide (e.g., as shown in FIGS. 1-4), in accordance with some applications of the present invention. For some applications, an anchoring system 140 is used to fix a pancreaticobiliary secretion-diversion guide in place within the gastrointestinal tract of a subject.

Typically, anchoring system 140 comprises one or more helical anchors 80 and anchoring mount 100. Anchor 80 is generally the same as anchor 80 described hereinabove. FIG. 5A shows anchor 80 deployed within the first section of duodenum 10, duodenal bulb 19. Anchor 80 pushes against the walls of duodenal bulb 19 and applies pressure to the wall of duodenal bulb 19 in order to fix a pancreaticobiliary secretion-diversion guide in place. Anchor 80 typically comprises retrieval element 82 described hereinabove with reference to FIG. 2A-B.

For some applications, anchor 80 is coupled to an anchoring mount 100. Anchoring mount 100 is typically deployed within the gastrointestinal tract, in a location that is downstream of helical anchor 80. Anchoring mount 100 typically comprises two or more, e.g., four, longitudinal struts 32, configured to be aligned in parallel with a longitudinal axis of the gastrointestinal tract. Longitudinal struts 32 typically contact the walls of the intestine in order to apply pressure to the walls and maintain a pancreaticobiliary secretion-diversion guide in place within the gastrointestinal tract of the subject.

Reference is made to FIGS. 6A-B, which are schematic illustrations of an alternative configuration of the anchoring system 140 for use with a pancreaticobiliary secretion-diversion guide (e.g., as shown in FIGS. 1-4), in accordance with an application of the present invention. For some applications anchoring system 140 further comprises an additional intragastric anchor 70. Intragastric anchor 70 is typically the same as intragastric anchor 70 described hereinabove.

Figure 7A:
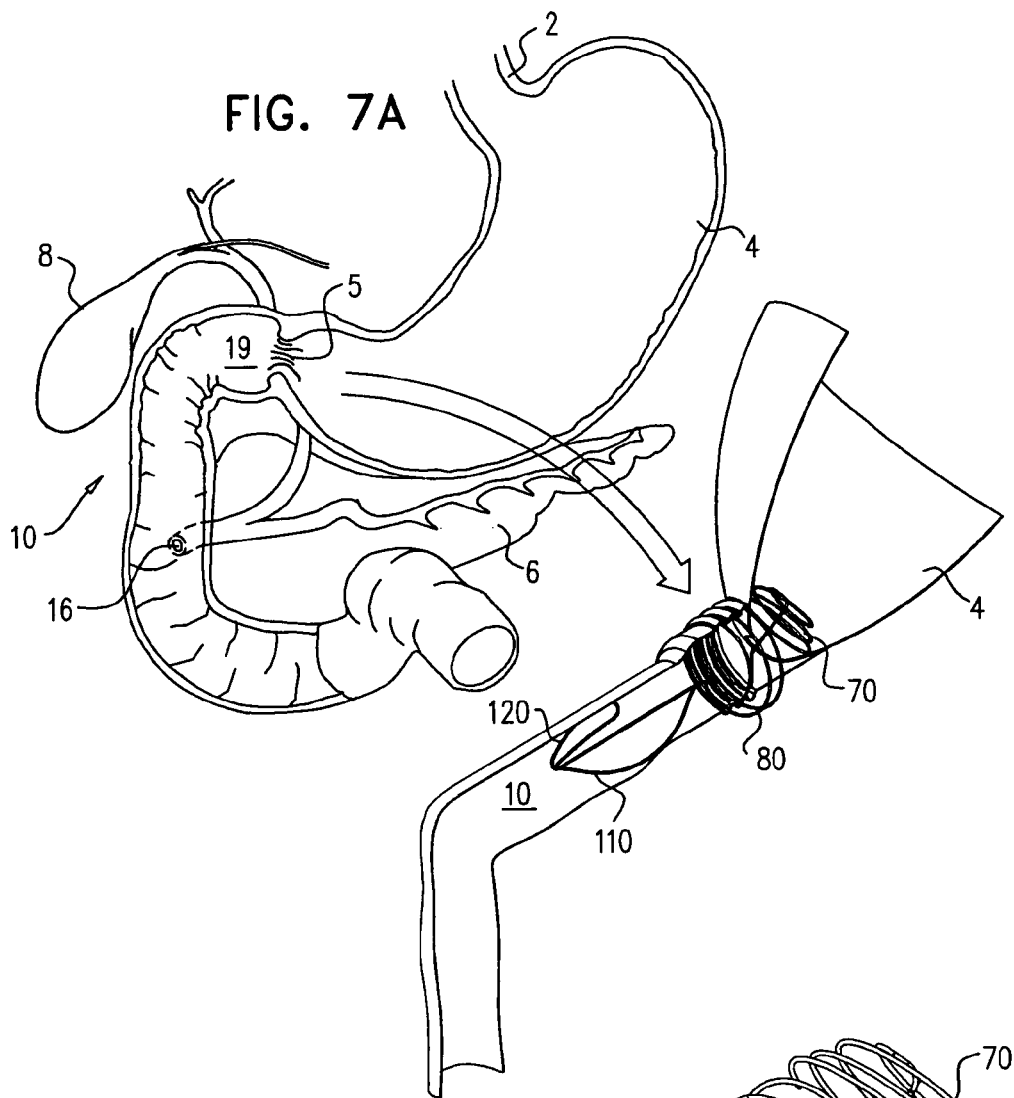
FIGS. 7A-B are schematic illustrations of an anchoring system for use with a pancreaticobiliary secretion-diversion guide, in accordance with an application of the present invention.
Figure 7B:
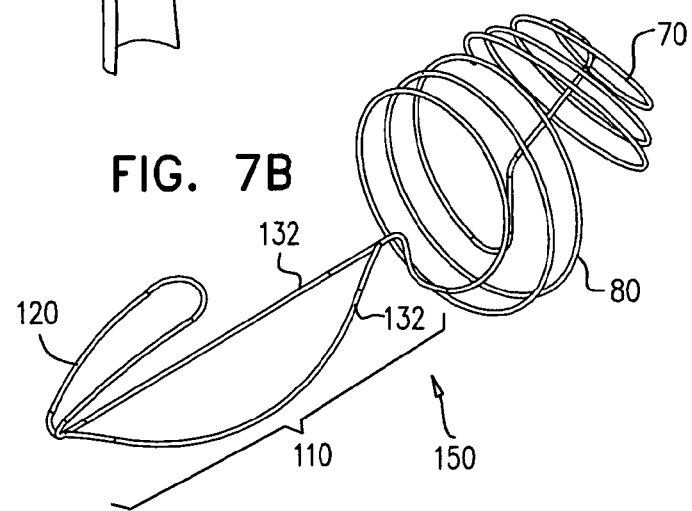

Reference is made to FIGS. 7A-B, which are schematic illustrations of anchoring system 150 for use with a pancreaticobiliary secretion-diversion guide (e.g., as shown in FIGS. 1-4), in accordance with some applications of the present invention. For some applications, anchoring system 150 is used to fix a pancreaticobiliary secretion-diversion guide in place within the gastrointestinal tract of a subject. Typically, anchoring system 150 comprises one or more helical anchors 80 and anchoring mount 110. Anchor 80 is generally the same as anchor 80 described hereinabove. FIG. 7A shows anchor 80 deployed within the first section of duodenum 10, duodenal bulb 19. Anchor 80 pushes against the walls of duodenal bulb 19 and applies pressure to the wall of duodenal bulb 19 in order to fix the pancreaticobiliary secretion-diversion guide in place.

For some applications, anchor 80 is coupled to an anchoring mount 110. Anchoring mount 110 is typically deployed within the gastrointestinal tract, in a location that is downstream of helical anchor 80. Anchoring mount 110 typically comprises two or more longitudinal struts 132. For some applications, at least one of struts 132 is configured to be aligned in parallel with a longitudinal axis of the gastrointestinal tract. For some applications, at least one of struts 132 is curved. FIG. 7A shows a curved strut 132 contacting the wall of the intestine in order to apply pressure to the wall and maintain a pancreaticobiliary secretion-diversion guide in place within the gastrointestinal tract of the subject.

Anchoring mount 110 typically comprises an additional flexible and elastic anchoring element 120. Element 120 typically contacts a wall of the intestine in order to apply pressure to the wall and maintain a pancreaticobiliary secretion-diversion guide in place within the gastrointestinal tract of the subject.

For some applications, anchoring system 150 further comprises an additional intragastric anchor 70. Intragastric anchor 70 is typically the same as intragastric anchor 70 described hereinabove. For some applications, anchors 70 and/or anchor 80 may comprise a retrieval element, e.g., similar to element 82 described hereinabove.

Figure 8A:
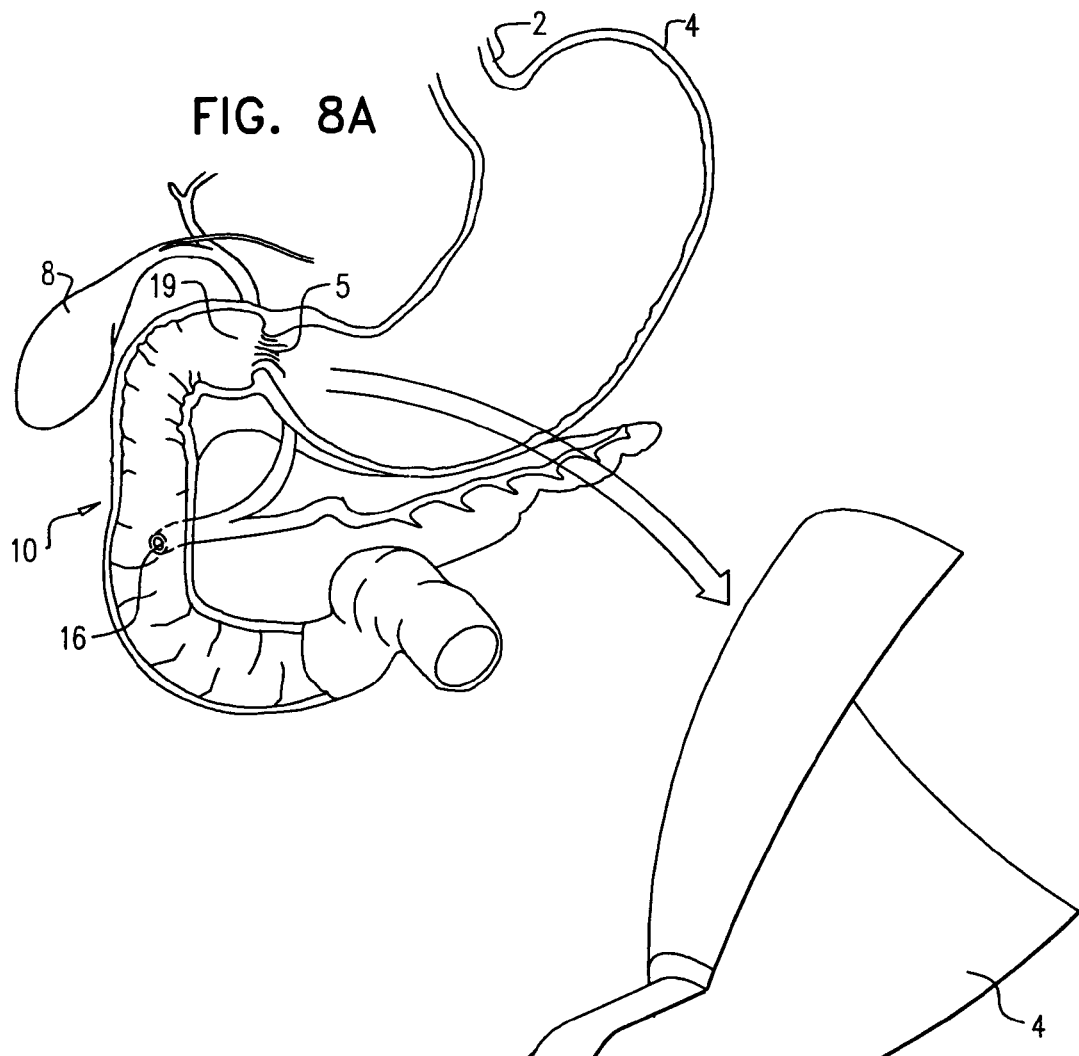
FIGS. 8A-B are schematic illustrations of a pancreaticobiliary secretion-diversion guide, in accordance with an application of the present invention.
Figure 8B:
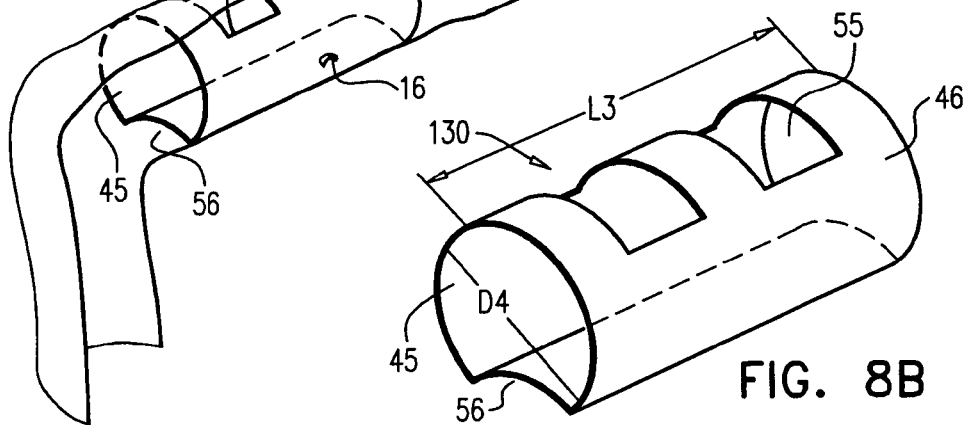

Reference is made to FIGS. 8A-B, which are schematic illustrations of a pancreaticobiliary secretion-diversion guide 130, in accordance with some applications of the present invention.

For some applications, pancreaticobiliary secretion-diversion guide 130 is shaped to define at least a portion of a tube, the tube comprising a tube wall, the tube wall having an inner surface 45 and an outer surface 46, the tube wall inner surface defining a lumen for passage of chyme therethrough. Typically the lumen of guide 130 has a characteristic diameter D4 of 20-35 mm, e.g., 25-30 mm (it being understood that guide 130 as shown in FIGS. 8A-B does not form a complete circle). Guide 130 typically has a length L3 of at least 60 cm, or less than 110 cm or between 60 and 110 cm. When deployed within the gastrointestinal tract of the subject, guide 130 typically extends from a location in duodenum 10 to an area that is in the upper or in the mid jejunum. Alternatively, guide 130 is of sufficient length in order to extend from a location in duodenum 10 to an area that is in the lower jejunum or the ileum of the small intestine.

The tube wall of guide 130 typically comprises an aperture portion, shaped to define one or more apertures 55, e.g., 1-5 or 5-50 apertures. For some applications, the apertures have a cross-sectional area of at least 1 cm2, although apertures of smaller cross-sectional area (i.e., less than 1 cm2) are also suitable for use in some applications of the present invention. When deployed within the gastrointestinal tract, typically within duodenum 10, guide 130 contacts the wall of the gastrointestinal tract of the subject, and apertures 55 provide contact between chyme within the lumen and the wall of the gastrointestinal tract.

The tube wall is further shaped to define a channel 56, which is configured to collect pancreaticobiliary secretions from an anatomical entry location into the gastrointestinal tract, e.g., duodenal papilla 16 and to inhibit contact of the pancreaticobiliary secretions with the food within the lumen of the tube.

Guide 130 is configured to collect pancreaticobiliary secretions from an anatomical entry location into duodenum 10, e.g., duodenal papilla 16, and deliver the pancreaticobiliary secretions to a location in the gastrointestinal tract that is distal to the duodenal papilla. For some applications, guide 130 transfers the pancreaticobiliary secretions to a location that is beyond the duodenum, e.g., beyond the ligament of Treitz which is the final section of the duodenum. For some applications, guide 130 diverts the pancreaticobiliary secretions to a location that is at least 40 cm or less than 80 cm, or between 40 and 80 cm beyond the ligament of Treitz.

Guide 130 is typically deployed within the gastrointestinal tract of the subject, such that channel 56 faces duodenal papilla 16. Guide 130 is typically disposed within duodenum 10 in a location that is in the vicinity of duodenal papilla 16, such that secretions entering the duodenum at papilla 16 are directly collected into channel 56 of guide 130. The pancreaticobiliary secretions flow through distally in channel 56 of guide 130, and are typically discharged from the channel in an area that is in the upper or in the mid jejunum of the small intestine.

Channel 56 of guide 130 generally inhibits contact between the pancreaticobiliary secretions and chyme passing within the guide lumen, thereby reducing emulsification and formation of micelles of ingested fat, and disrupting the process of fat digestion in the body.

Figure 9A:
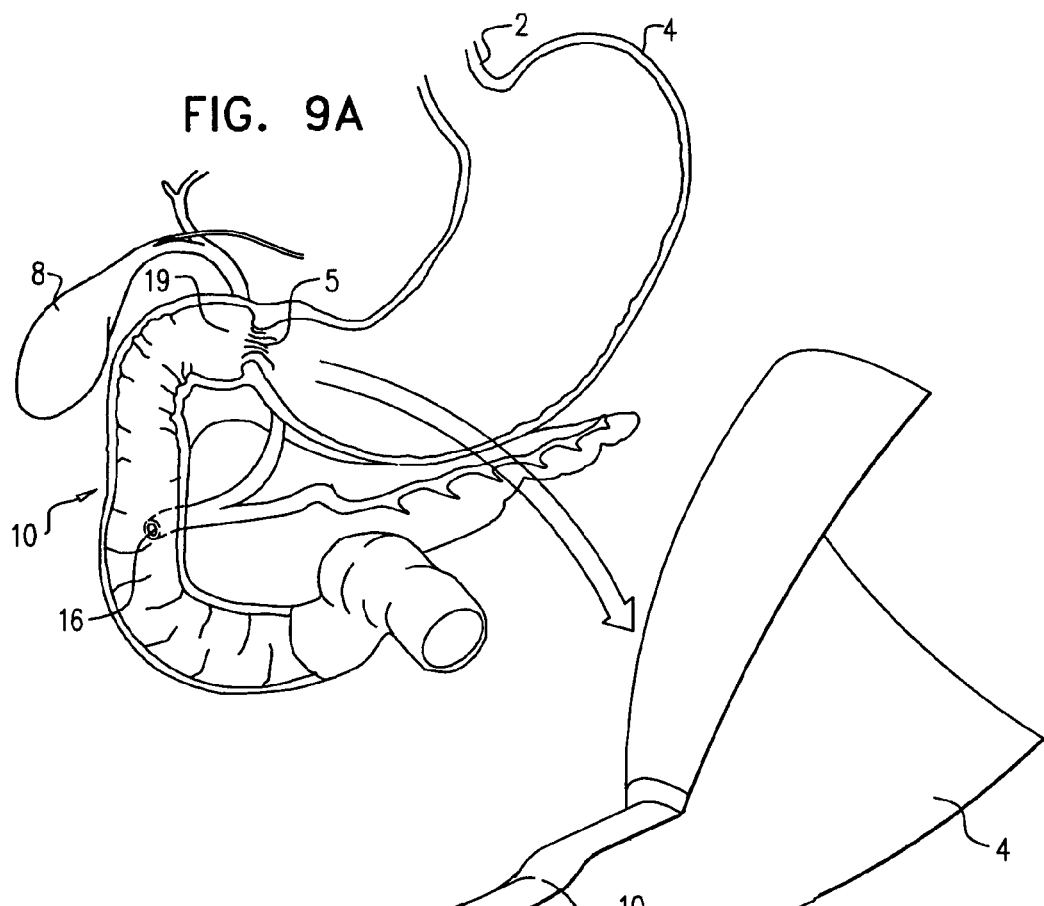
FIGS. 9A-B are schematic illustrations of a pancreaticobiliary secretion-diversion guide, in accordance with an application of the present invention.
Figure 9B:
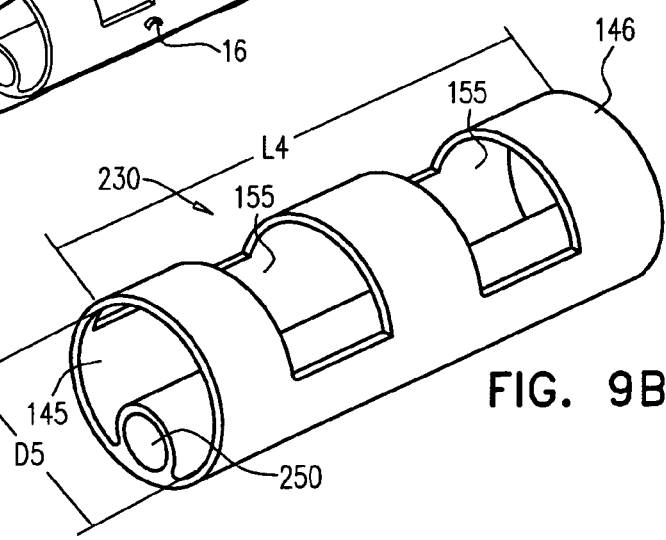

Reference is made to FIGS. 9A-B, which are schematic illustrations of a pancreaticobiliary secretion-diversion guide 230, in accordance with some applications of the present invention. For some applications, pancreaticobiliary secretion-diversion guide 230 is shaped to define at least a portion of a tube, the tube comprising a tube wall, the tube wall having an inner surface 145 and an outer surface 146, the tube wall inner surface defining a lumen for passage of chyme therethrough. Typically the lumen of guide 230 has a characteristic diameter D5 of 20-35 mm, e.g., 25-30 mm. Guide 230 typically has a length L4 of at least 60 cm, or less than 110 cm or between 60 and 110 cm. When deployed within the gastrointestinal tract of the subject, guide 230 typically extends from a location in duodenum 10 to an area that is in the upper or in the mid jejunum. Alternatively, guide 130 is of sufficient length in order to extend from a location in duodenum 10 to an area that is in the lower jejunum or the ileum of the small intestine.

The tube wall of guide 230 typically comprises an aperture portion, shaped to define one or more apertures 155, e.g., 1-5 or 5-50 apertures 155. When deployed within the gastrointestinal tract, typically within duodenum 10, guide 230 contacts the wall of the gastrointestinal tract of the subject, and apertures 155 provide contact between chyme within the lumen and the wall of the gastrointestinal tract. For some applications, the apertures have a cross-sectional area of at least 1 cm2, although apertures of smaller cross-sectional area (i.e., less than 1 cm2) also are suitable for use in some applications of the present invention. Typically, guide 230 makes contact with a complete circumference of the duodenum.

For some applications, inner surface 145 of the tube wall of guide 230 is coupled to an additional inner tube 250. Typically, tube 250 is shaped to define a tube lumen configured for passage of pancreaticobiliary secretions therethrough. Tube 250 is typically shaped to define an orifice in a lateral wall of the lumen (not shown) having a diameter of 5-20 mm, e.g., 10-20 mm, which is configured to collect pancreaticobiliary secretions from an anatomical entry location into the gastrointestinal tract, e.g., duodenal papilla 16, and to inhibit contact of the pancreaticobiliary secretions with the chyme within the lumen of the tube. For such applications, the orifice has a diameter that is sufficient in size to surround at least the entire diameter of the duodenal papilla.

For some applications, inner tube 250 has a length of at least 60 cm, or less than 110 cm, or between 60 and 110 cm. Inner tube 250 is configured to collect pancreaticobiliary secretions from an anatomical entry location into duodenum 10, e.g., duodenal papilla 16, and deliver the pancreaticobiliary secretions to a location in the gastrointestinal tract that is distal to the duodenal papilla. For some applications, guide 230 transfers the pancreaticobiliary secretions to a location that is beyond the duodenum, e.g., beyond the ligament of Treitz. For some applications, guide 230 diverts the pancreaticobiliary secretions to a location that is at least 40 or less than 80 cm, or between 40 and 80 cm beyond the ligament of Treitz.

Guide 230 is typically deployed within the gastrointestinal tract of the subject, such that the orifice of inner tube 250 faces duodenal papilla 16. Guide 230 is typically disposed within duodenum 10 in a location that is in the vicinity of duodenal papilla 16, such that secretions entering the duodenum at papilla 16 are directly collected into tube 250 of guide 230. The pancreaticobiliary secretions flow distally in tube 250 of guide 130, and are typically discharged from the tube in an area that is in the upper or in the mid jejunum. Alternatively, tube 250 is of sufficient length in order to deliver the pancreaticobiliary secretions to an area that is in the lower jejunum or the ileum of the small intestine.

Inner tube 250 of guide 230 generally inhibits contact between the pancreaticobiliary secretions and chyme passing within the guide lumen, thereby reducing emulsification and formation of micelles of ingested fat, and disrupting the process of fat digestion in the body.

For some applications, a pancreaticobiliary secretion diversion guide as described for example with reference to FIG. 1, or parts thereof, is used in combination with guide 230. For example, guide 30 (described with reference to FIG. 1) may replace inner tube 250 (configurations not shown).

Figure 10A:
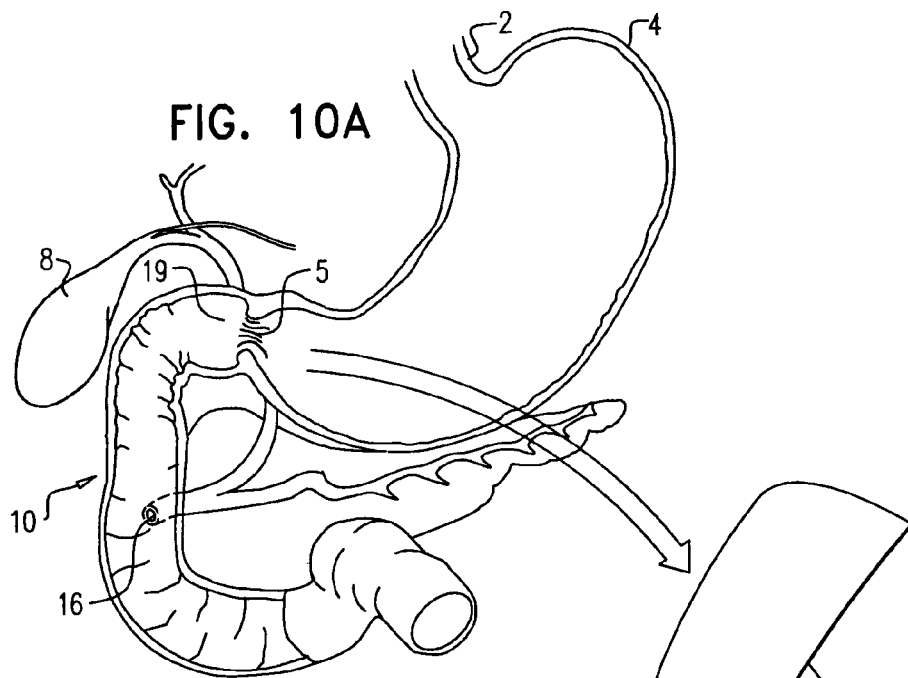
FIGS. 10A-B are schematic illustrations of a pancreaticobiliary secretion-diversion guide, in accordance with an application of the present invention.
Figure 10B:
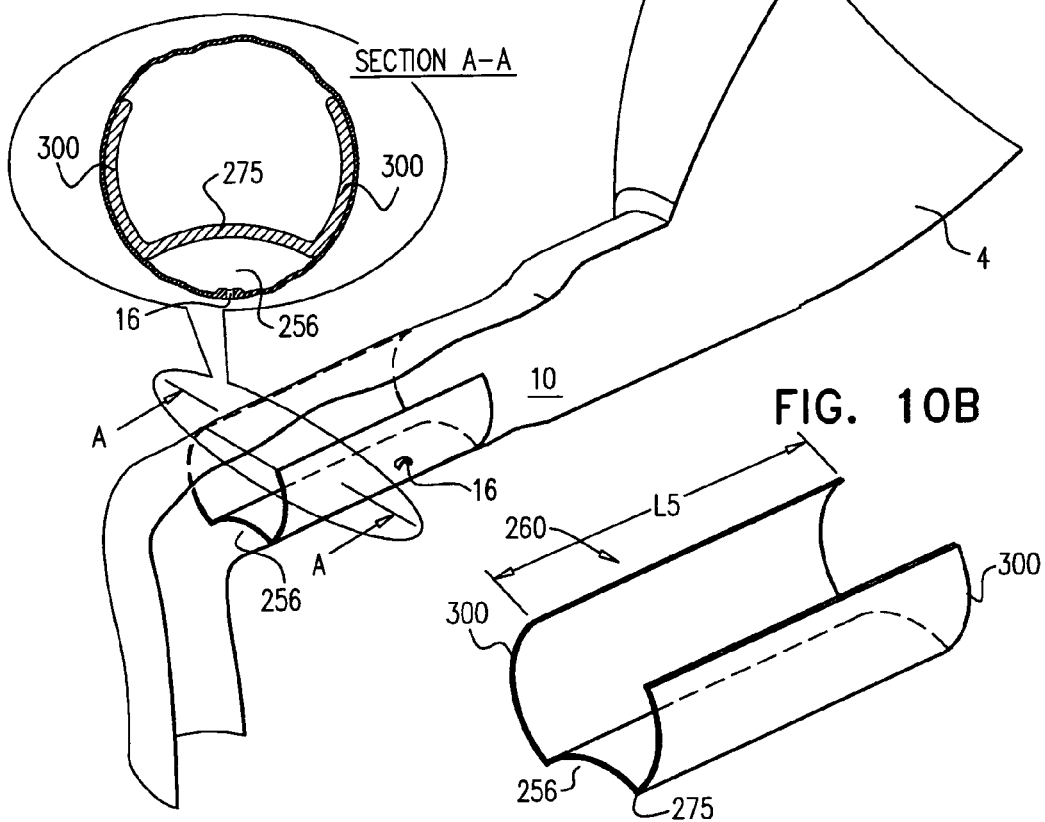

Reference is made to FIGS. 10A-B, which are schematic illustrations of a pancreaticobiliary secretion-diversion guide 260, in accordance with some applications of the present invention. For some applications, pancreaticobiliary secretion-diversion guide 260 comprises a guide body 275 having an inner surface and an outer surface. The outer surface of the guide body is typically shaped to define a channel 256, which is configured to collect pancreaticobiliary secretions from an anatomical entry location into the gastrointestinal tract, e.g., duodenal papilla 16 and to inhibit contact of the pancreaticobiliary secretions with the chyme within the duodenum. The chyme passing through duodenum 10 typically comes in contact with the inner surface of guide body 275.

Guide 260 is typically deployed within the gastrointestinal tract of the subject, such that channel 256 faces duodenal papilla 16. Guide 260 is typically disposed within duodenum 10 in a location that is in the vicinity of duodenal papilla 16, such that secretions entering the duodenum at papilla 16 are directly collected into channel 256 of guide 260. The pancreaticobiliary secretions flow through distally in channel 256 of guide 260, and are typically discharged from the channel in an area that is distal to the duodenal papilla. For some applications, the secretions are discharged in the upper or in the mid jejunum of the small intestine. For some applications, the pancreaticobiliary secretions are discharged in a location that is at least 40 cm or less than 80 cm, or between 40 and 80 cm beyond the ligament of Treitz.

Channel 256 and guide body 275 of guide 260 generally inhibit contact between the pancreaticobiliary secretions and chyme passing within the duodenum, thereby reducing emulsification and formation of micelles of ingested fat, and disrupting the process of fat digestion in the body.

Guide 260 typically has a length L5 of at least 60 cm, or less than 110 cm or between 60 and 110 cm. When deployed within the gastrointestinal tract of the subject, guide 230 typically extends from a location in duodenum 10 to an area that is in the upper or in the mid jejunum. Alternatively, guide 260 is of sufficient length in order to extend from a location in duodenum 10 to an area that is in the lower jejunum or the ileum of the small intestine.

Guide 260 comprises one or more arms 300, coupled to the guide body, and configured to apply pressure to the wall of the gastrointestinal tract in order to maintain the pancreaticobiliary secretion-diversion guide in place within the intestine.

Reference is made to FIG. 10A which includes a cross-sectional schematic illustration, indicated by A, of guide 260 when deployed within a gastrointestinal tract of the subject. Arms 300 are shown pressing against a section of the intestine wall and applying an outward force to the intestine in order to maintain guide 260 in place.

Reference is made to FIGS. 1A-C, 2A-B, 3A-B, 4A-B, 5A-B, 6A-B, 7A-B, 8A-B, 9A-B, and 10A-B. The apparatus for use with pancreaticobiliary secretions which is described herein may be surrounded by a facilitating sleeve during implantation. For some applications, a sleeve (not shown) surrounds all or some of the components of the apparatus, e.g., the anchoring system and/or the pancreaticobiliary secretion-diversion guide. Typically, the sleeve facilitates insertion of the apparatus for use with pancreaticobiliary secretions into a gastrointestinal tract of a subject.

Reference is still made to FIGS. 1A-C, 2A-B, 3A-B, 4A-B, 5A-B, 6A-B, 7A-B, 8A-B, 9A-B, and 10A-B. Components of the apparatus described herein, e.g., the anchoring system and/or the pancreaticobiliary secretion-diversion guide, typically but not necessarily comprise a shape memory alloy such as nitinol or stainless steel. For some applications, components of the apparatus described herein may comprise or be coated with a biocompatible and biologically inert material such as polytetrafluoroethylene (PTFE) and/or silicone. For example, components of the anchoring system may be further surrounded by a silicone sheath which is configured to apply pressure to the wall of the gastrointestinal tract in order to maintain the pancreaticobiliary secretion-diversion guide in place. For some applications, the silicone sheath is inflated with a fluid, i.e., a gas or a liquid.

Typically, the apparatus described herein generally comprises a material with low permeability. For some applications, the apparatus material or coating provides a generally low coefficient of friction, e.g., less than 0.3.

For some applications, the apparatus described herein may be used as a drug delivery tool. The apparatus may comprise in its body, or be coated with, a substance, such as but not limited to, a medication (e.g., an antibiotic and/or an anti-inflammatory medication), a hormone, a bile acid resin, and/or another binder.

For some applications, one or more components of the apparatus described herein, e.g., the anchoring system and/or the pancreaticobiliary secretion-diversion guide, may comprise a biodegradable material, e.g., a biodegradable polymer, which gradually degrades, allowing the apparatus to leave the body.

For some applications, the apparatus described herein is configured to prevent tissue growth on an exterior surface of the apparatus (e.g., using a chemical coating on the exterior surface).

For some applications, a marker may be coupled to any component of the apparatus described herein, in order to enable detection by fluoroscopic imaging of the position and orientation of the apparatus within the gastrointestinal tract.

Reference is still made to FIGS. 1A-C, 2A-B, 3A-B, 4A-B, 5A-B, 6A-B, 7A-B, 8A-B, 9A-B, and 10A-B. Components of the apparatus described herein, e.g., the anchoring system and/or the pancreaticobiliary secretion-diversion guide, are configured for endoscopic deployment and retrieval and are typically inserted into the digestive tract of a subject using minimally invasive techniques such as endoscopy and/or endoscopic overtubing. Alternatively, components of the apparatus described herein, e.g., the anchoring system and/or the pancreaticobiliary secretion-diversion guide, may be deployed within the digestive tract by means of invasive surgery.

For some applications, the apparatus described herein may comprise fiber optics, biopsy tools, optical devices (e.g., a CCD camera) and/or other imaging devices.

Reference is still made to FIGS. 1A-C, 2A-B, 3A-B, 4A-B, 5A-B, 6A-B, 7A-B, 8A-B, 9A-B, and 10A-B. For some applications, the pancreaticobiliary secretion-diversion guide affects hormonal secretion and/or action. Many hormones and enzymes participate in the digestion process, some of which are released by the gastrointestinal tract, for example, (a) GIP (Glucose-dependent insulinotropic peptide), a digestive hormone which is synthesized by intestinal K cells, and (b) GLP-1 (Glucagon-like peptide-1), which is synthesized by intestinal L cells. These hormones typically play a role in the regulation of the digestive process, and may affect fat metabolism and insulin secretion and action. Some applications of the present invention may modify the secretion and/or the action of these hormones and consequently modify the digestive process (including but not limited to fat metabolism and insulin secretion and action).

Additionally or alternatively, the apparatus described herein or components thereof may trigger a sense of satiety in a subject. Typically, mechanoreceptors that are present in the stomach and proximal small intestine are sensitive to mechanical changes in theses areas (e.g., pressure and/or stretching) that are usually caused by food passing through the gastrointestinal tract. Theses mechanical changes trigger a signal which leads to a sensation of satiety in the subject and as a result affects the appetite of the subject. For some applications, the apparatus described herein, or components thereof, are configured to contact and/or stretch and/or apply mechanical pressure to a portion of the gastrointestinal tract. Thus, the apparatus described herein may activate mechanoreceptors in the gastrointestinal tract leading to a sense of satiety and, as a result, limit food intake by the subject.

Accordingly, the pancreaticobiliary secretion-diversion guide as described herein is typically used for treatment of obesity, type II diabetes and other disease such as non-alcoholic fatty liver disease and/or non-alcoholic steatohepatitis.

Reference is made to the anchoring systems described in FIGS. 1A-C, 2A-B, 3A-B, 4A-B, 5A-B, 6A-B, and 7A-B. For some applications, the anchoring systems described herein may be used for other implantable devices, including but not limited to, a bariatric sleeve. For some applications, the anchoring systems may be implanted for purposes of dilating areas in the gastrointestinal tract, e.g., in a patient with a constricted gastrointestinal tract due to cancer.

Additionally or alternatively, the anchoring systems described herein may be implanted for drug delivery purposes in any suitable location within the gastrointestinal tract. For example, the anchoring system may be implanted in the terminal ileum or any other region of the small or large intestine. For example, the anchors may release a drug for localized treatment of, e.g., neoplasia or an intestinal inflammatory disease, e.g., Crohn's disease or ulcerative colitis.

Reference is still made to the anchoring systems described with reference to FIGS. 1A-C, 2A-B, 3A-B, 4A-B, 5A-B, 6A-B, and 7A-B. For some applications, the anchoring system additionally or alternatively comprises tissue-penetrating anchors which penetrate tissue of the gastrointestinal tract in order to enhance anchoring of the secretion-diversion guide in the gastrointestinal tract. Typically the tissue-penetrating anchors are coupled to components of the anchoring system and/or to components of the secretion-diversion guide. The tissue-penetrating anchors are typically shaped to define any suitable shape, e.g., barbs, hooks, and/or spikes.

Although techniques of the present invention have generally been described herein as being applied to the stomach and small intestine, these techniques may additionally be used, mutatis mutandis, to treat other lumens of the gastrointestinal tract of a subject, such as the esophagus, or the large intestine.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   providing apparatus for use with pancreaticobiliary secretions that enter a gastrointestinal tract of a subject at an anatomical entry location, the apparatus comprising:
      a pancreaticobiliary secretion-diversion guide configured to collect pancreaticobiliary secretions secreted from the anatomical entry location and deliver the pancreaticobiliary secretions to a location in the gastrointestinal tract that is distal to the anatomical entry location; and
      an anchoring system configured to apply pressure to a wall of the gastrointestinal tract in order to maintain the pancreaticobiliary secretion-diversion guide in place, the anchoring system comprising:
         one or more anchors; and
         at least one anchoring mount configured to be located in the gastrointestinal tract, downstream of the one or more anchors, the anchoring mount comprising a curved longitudinal strut; and
   deploying the apparatus within the gastrointestinal tract of the subject such that:
      the one or more anchors of the anchoring system are disposed upstream of the entry location of pancreaticobiliary secretions into the gastrointestinal tract; and
      the curved longitudinal strut contacts the wall of the gastrointestinal tract by extending asymmetrically towards one side of the gastrointestinal tract to apply pressure thereto.

2. The method according to claim 1,
   wherein the anatomical entry location includes a duodenal papilla of the subject, and
   wherein deploying the apparatus comprises deploying the apparatus such that the one or more anchors disposed upstream of the entry location are disposed upstream of the papilla.

3. The method according to claim 2, the method further comprising positioning the pancreaticobiliary secretion-diversion guide to collect the pancreaticobiliary secretions that are secreted from the duodenal papilla, without placing the pancreaticobiliary secretion-diversion guide in an anatomical site through which the secretions pass, the anatomical site selected from the group consisting of: a duodenal papilla and a common bile duct of the subject.

4. The method according to claim 1, wherein deploying the apparatus comprises positioning the pancreaticobiliary secretion-diversion guide to collect the pancreaticobiliary secretions and deliver the pancreaticobiliary secretions to a location that is beyond a ligament of Treitz of the subject.

5. The method according to claim 1, wherein the method comprises positioning the pancreaticobiliary secretion-diversion guide such as to prevent the pancreaticobiliary secretions from contacting chyme in a portion of the gastrointestinal tract.

6. The method according to claim 1, wherein providing the pancreaticobiliary secretion-diversion guide comprises providing the pancreaticobiliary secretion-diversion guide having a proximal end at a proximal portion thereof and a distal end at a distal portion thereof, the proximal portion having a cross section of 10-100 mm$^2$, 10 mm from the proximal end, the distal portion having a cross section of 5-100 mm$^2$, 10 mm from the distal end, the cross section of the proximal portion being at least two times greater than the cross section of the distal portion.

7. The method according to claim 6, wherein providing the pancreaticobiliary secretion-diversion guide comprises providing the pancreaticobiliary secretion-diversion guide, the proximal portion having a width of 5-25 mm.

8. The method according to claim 6, wherein providing the pancreaticobiliary secretion-diversion guide comprises providing the pancreaticobiliary secretion-diversion guide, the distal portion having a length of 50-110 cm extending from a proximal end thereof to the distal end thereof.

9. The method according to claim 1, wherein deploying the apparatus within the gastrointestinal tract comprises deploying the one or more anchors such that they are disposed entirely within the lumen of the gastrointestinal tract, and do not penetrate tissue of the gastrointestinal tract.

10. The method according to claim 1, wherein the method comprises providing the one or more anchors each having a diameter of 20-35 mm when unconstrained.

11. The method according to claim 1, wherein deploying the one or more anchors upstream of the entry location comprises deploying the one or more anchors within a duodenal bulb of the subject.

12. The method according to claim 1, wherein providing the apparatus comprises providing the anchoring system, in which at least a portion of the anchoring system is surrounded with a silicone sheath configured to apply pressure to the wall of the gastrointestinal tract in order to maintain the pancreaticobiliary secretion-diversion guide in place.

13. The method according claim 1, further comprising implanting an intragastric anchor, coupled to the guide, in a pyloric antrum of a stomach of a subject, the intragastric anchor configured to apply pressure to a wall of the stomach in order to maintain the guide in place.

14. The method according to claim 13, wherein implanting the intragastric anchor comprises implanting a helical intragastric anchor.

15. The method according to claim 13, wherein implanting the intragastric anchor comprises implanting an intragastric anchor having a longest dimension of 35-55 mm.

16. The method according to claim 1, wherein providing the apparatus comprises providing the apparatus, the one or more anchors being flexible.

17. The method according to claim 1, wherein the method comprises positioning the one or more anchors at a non-perpendicular angle with respect to a longitudinal axis of the pancreaticobiliary secretion-diversion guide.

18. The method according to claim 1,
   wherein providing the apparatus comprises providing the anchoring system, and
   wherein the one or more anchors comprise one or more helical anchors.

19. The method according to claim 1,
   wherein providing the apparatus comprises providing the anchoring mount further comprising a longitudinal strut, and
   wherein deploying the apparatus comprises deploying the longitudinal strut such that the longitudinal strut is aligned in parallel with a longitudinal axis of the gastrointestinal tract.

20. An apparatus for use with pancreaticobiliary secretions that enter a gastrointestinal tract of a subject at an anatomical entry location, the apparatus comprising:
   a pancreaticobiliary secretion-diversion guide configured to collect the pancreaticobiliary secretions from the anatomical entry location and deliver the pancreaticobiliary secretions to a location in the gastrointestinal tract that is distal to the anatomical entry location; and
   an anchoring system comprising:
      one or more anchors configured to be located within the gastrointestinal tract and configured to apply pressure to a wall of the gastrointestinal tract in order to maintain the pancreaticobiliary secretion-diversion guide in place; and at least one anchoring mount configured to be located in the gastrointestinal tract, downstream of the one or more anchors, the anchoring mount comprising a curved longitudinal strut configured to contact the wall of the gastrointestinal tract by extending asymmetrically towards one side of the gastrointestinal tract to apply pressure thereto.

21. The apparatus according to claim 20, wherein the one or more anchors comprise one or more helical anchors.

22. The apparatus according to claim 20 wherein the anchoring mount further comprises a longitudinal strut configured to be aligned in parallel with a longitudinal axis of the gastrointestinal tract.

23. The apparatus according to claim 22, wherein the intragastric anchor has a longest dimension of 35-55 mm.

24. The apparatus according to claim 20, further comprising an intragastric anchor configured to be located in a pyloric antrum of a stomach of the subject and configured to apply pressure to a wall of the stomach in order to maintain the pancreaticobiliary secretion-diversion guide in place.

* * * * *